(12) United States Patent
Nakamitsu et al.

(10) Patent No.: US 11,311,176 B2
(45) Date of Patent: Apr. 26, 2022

(54) ENDOSCOPE INSERTION OBSERVATION APPARATUS CAPABLE OF CALCULATING DURATION OF MOVEMENT OF INSERTION PORTION

(71) Applicant: OLYMPUS CORPORATION, Hachioji (JP)

(72) Inventors: Takechiyo Nakamitsu, Hachioji (JP); Kensuke Miyake, Hamura (JP); Akira Murata, Inagi (JP); Isamu Nakajima, Sagamiahara (JP)

(73) Assignee: OLYMPUS CORPORATION, Tokyo (JP)

( * ) Notice: Subject to any disclaimer, the term of this patent is extended or adjusted under 35 U.S.C. 154(b) by 419 days.

(21) Appl. No.: 16/438,953

(22) Filed: Jun. 12, 2019

(65) Prior Publication Data
US 2019/0290108 A1    Sep. 26, 2019

Related U.S. Application Data

(63) Continuation of application No. PCT/JP2017/035874, filed on Oct. 2, 2017.

(30) Foreign Application Priority Data

Dec. 22, 2016    (JP) .............................. JP2016-249114

(51) Int. Cl.
*A61B 1/00* (2006.01)
*A61B 1/31* (2006.01)
(Continued)

(52) U.S. Cl.
CPC ............ *A61B 1/00147* (2013.01); *A61B 1/00* (2013.01); *A61B 1/00006* (2013.01);
(Continued)

(58) Field of Classification Search
None
See application file for complete search history.

(56) References Cited

U.S. PATENT DOCUMENTS

2008/0303898 A1* 12/2008 Nishimura ........... A61B 1/0005
348/65
2013/0261392 A1   10/2013 Yamamoto et al.
(Continued)

FOREIGN PATENT DOCUMENTS

JP    408-000542 A    1/1996
JP    2004-358095 A   12/2004
(Continued)

OTHER PUBLICATIONS

Dec. 5, 2017 International Search Report issued in International Patent Application No. PCT/JP2017/035874.

*Primary Examiner* — John P Leubecker
(74) *Attorney, Agent, or Firm* — Oliff PLC

(57) ABSTRACT

An endoscope insertion observation apparatus includes a processor designed to perform functions including: detecting an insertion state of an insertion portion of an endoscope that is insertable into and extractable from a subject; determining whether or not the insertion portion has reached a second site in the subject from a first site in the subject and/or whether the insertion portion has reached the first site from the second site in the subject based on a detection result of the insertion state; and calculating a duration of movement of the insertion portion from the first site to the second site after determining that the insertion portion has reached the second site, or a duration of movement of the insertion portion from the second site to the first site after determining that the insertion portion has reached the first site.

18 Claims, 29 Drawing Sheets

(51) Int. Cl.
  *A61B 1/04*   (2006.01)
  *A61B 1/06*   (2006.01)
  *A61B 1/045*  (2006.01)
  *G02B 23/24*  (2006.01)
  *A61B 1/01*   (2006.01)

(52) U.S. Cl.
  CPC .............. *A61B 1/0008* (2013.01); *A61B 1/04* (2013.01); *A61B 1/045* (2013.01); *A61B 1/0676* (2013.01); *G02B 23/24* (2013.01); *A61B 1/01* (2013.01); *A61B 1/31* (2013.01); *G02B 23/2446* (2013.01)

(56) References Cited

U.S. PATENT DOCUMENTS

2015/0313445 A1* 11/2015 Davidson ........... A61B 1/00006
                                                                    600/109
2016/0206381 A1*  7/2016 Grass .................... A61B 34/20
2017/0281049 A1  10/2017 Yamamoto et al.

FOREIGN PATENT DOCUMENTS

| JP | 2006-296576 A | 11/2006 |
| JP | 2012/115521 A | 6/2012 |
| WO | 2012/074016 A1 | 6/2012 |
| WO | 2016/098251 A1 | 6/2016 |
| WO | 2016/135966 A1 | 9/2016 |

\* cited by examiner

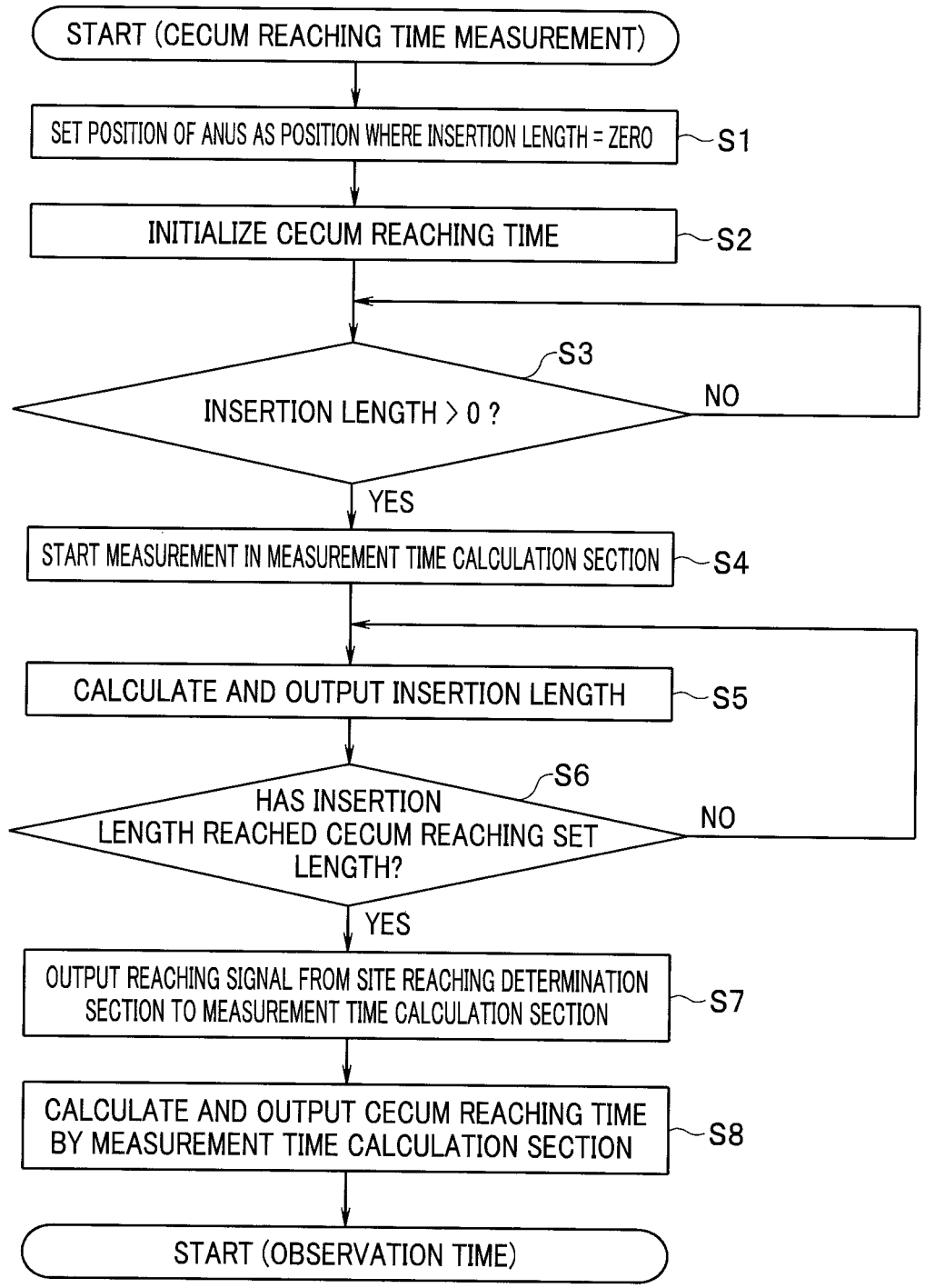

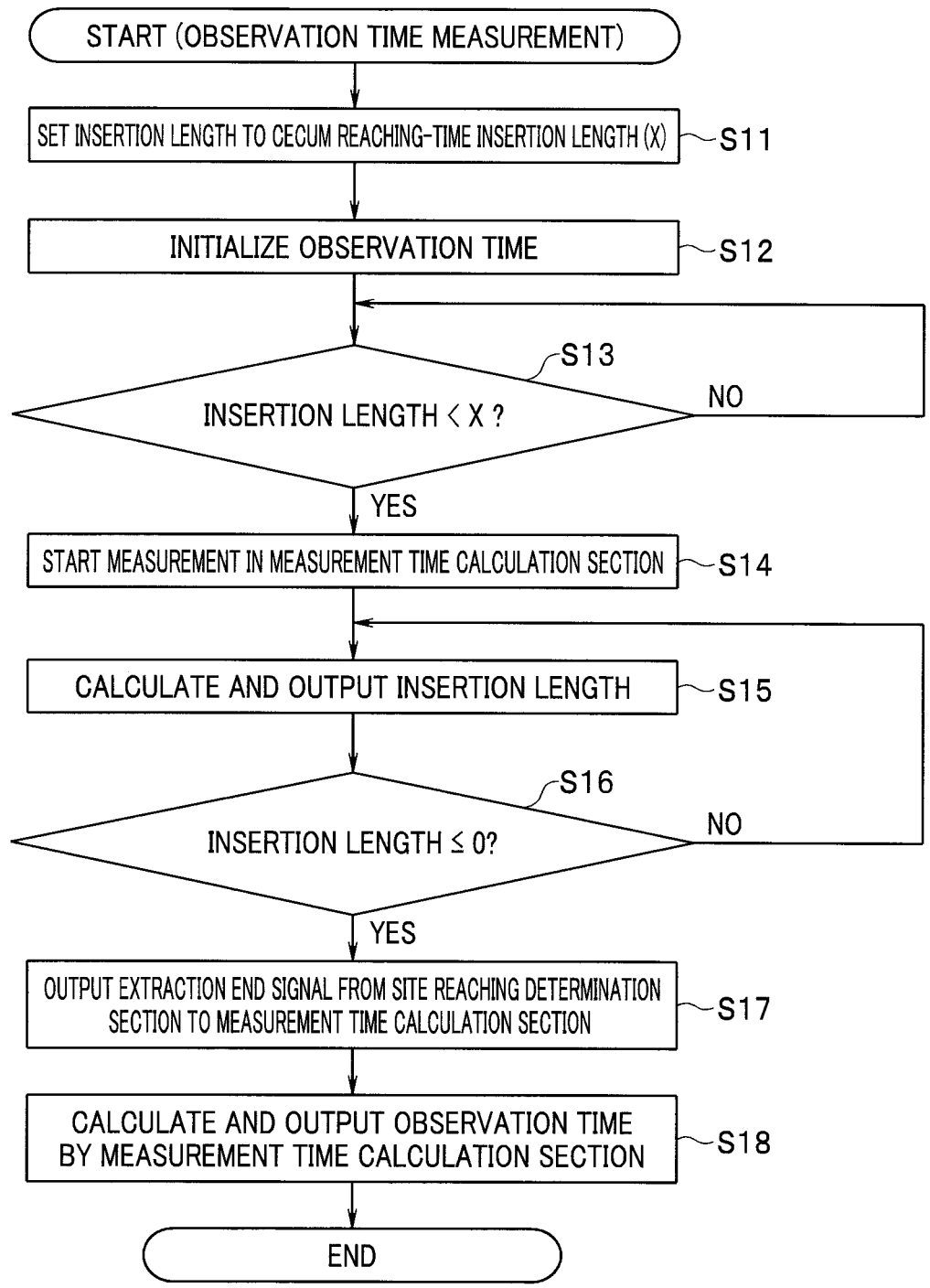

| SITE | INSERTION LENGTH | INSERTION STANDARD TIME | EXTRACTION STANDARD TIME |
|---|---|---|---|
| V0 | 15 | 10 | 10 |
| V1 | 30 | 20 | 30 |
| ⋮ | ⋮ | ⋮ | ⋮ |
| V7 | 70 | 10 | 20 |

| SITE | INSERTION LENGTH | DURING-INSERTION UPPER LIMIT NUMBER OF TIMES | DURING-EXTRACTION LOWER LIMIT NUMBER OF TIMES |
|---|---|---|---|
| V0 | 15 | 10 | 3 |
| V1 | 30 | 20 | 15 |
| ⋮ | ⋮ | ⋮ | ⋮ |
| V7 | 70 | 20 | 5 |

ENDOSCOPE INSERTION OBSERVATION APPARATUS CAPABLE OF CALCULATING DURATION OF MOVEMENT OF INSERTION PORTION

This application is a continuation application of PCT/W2017/035874 filed on Oct. 2, 2017 and claims benefit of Japanese Application No. 2016-249114 filed in Japan on Dec. 22, 2016, the entire contents of which are incorporated herein by this reference.

BACKGROUND

Exemplary embodiments relate to an endoscope insertion observation apparatus configured to observe an insertion state of an endoscope.

Conventionally, endoscope apparatuses have been widely used in medical fields. An endoscope apparatus is a medical instrument including an elongated insertion portion having flexibility, and an operator is capable of observing inside of a subject by inserting the insertion portion of the medical instrument into the subject. An endoscopic image of an inside of the subject, which is picked up by an endoscope, can be displayed on a monitor. However, it is impossible to know, from such an endoscopic image, how an insertion portion of an endoscope is inserted into a subject.

An endoscope insertion shape observation apparatus may be used as an apparatus that enables an insertion state of an endoscope to be known at the time of insertion of the endoscope. However, it can be difficult for an operator to easily understand the progression of insertion state.

In recent years, efforts for reducing disparity in medical techniques have been made, and guidelines and indicators are being formulated in a medical treatment of colon cancer, for example. As examination indicators in a colonoscopy, a cecum reaching time and observation time (extraction time) may be set, for example.

In order to comply with such examination indicators, it is necessary to measure a time required for each of the procedures during the actual examination. For example, regarding the cecum reaching time, the time from the insertion start clock time at which an insertion portion of an endoscope is inserted into the anus until the clock time at which the insertion portion reaches the cecum is measured. The operator may measure the cecum reaching time using a stopwatch, for example. However, such manual time measurements are frequently inaccurate, for example, due to inconsistencies in the determination of when the cecum has been reached.

SUMMARY

An endoscope insertion observation apparatus according to one aspect of the present disclosure includes a processor configured to: detect an insertion state of an insertion portion configured to be inserted into and extracted from a subject; determine whether the insertion portion has reached a second site in the subject from a first site in the subject and/or determine whether the insertion portion has reached the first site from the second site in the subject based on a result of the detection of the insertion state; and calculate a duration of movement of the insertion portion from the first site to the second site after determining that the insertion portion has reached the second site, and/or a duration of movement of the insertion portion from the second site to the first site after determining that the insertion portion has reached the first site.

BRIEF DESCRIPTION OF THE DRAWINGS

FIG. 8 is a flowchart illustrating an operation for obtaining a cecum reaching time according to an exemplary embodiment.

FIG. 9 is a flowchart illustrating an operation for obtaining an observation time according to an exemplary embodiment.

DETAILED DESCRIPTION

Hereinafter, embodiments of the present disclosure will be described in detail with reference to drawings.

Figure 1:
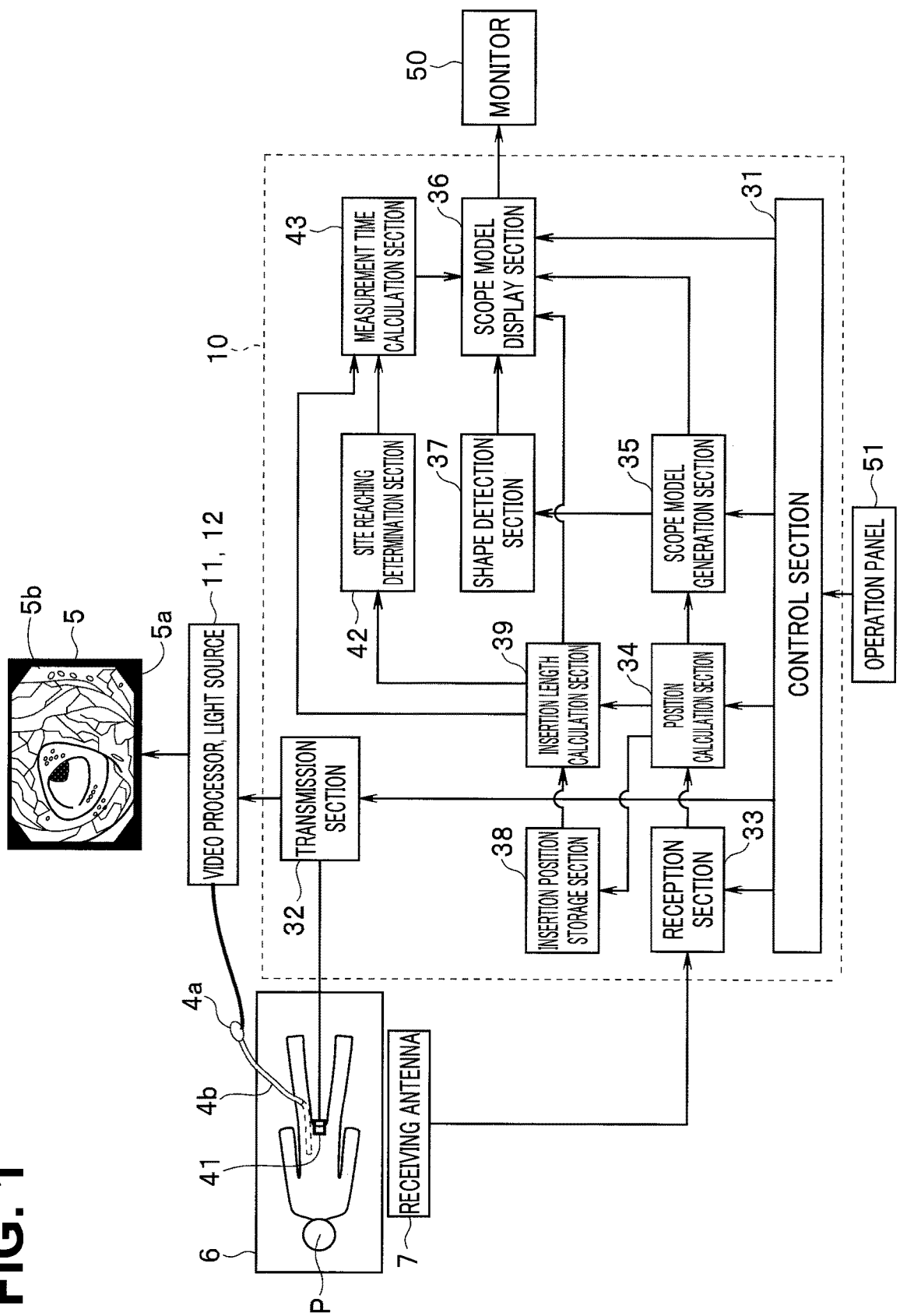
FIG. 1 is a block diagram illustrating an endoscope insertion observation apparatus according to an exemplary embodiment.
Figure 2:
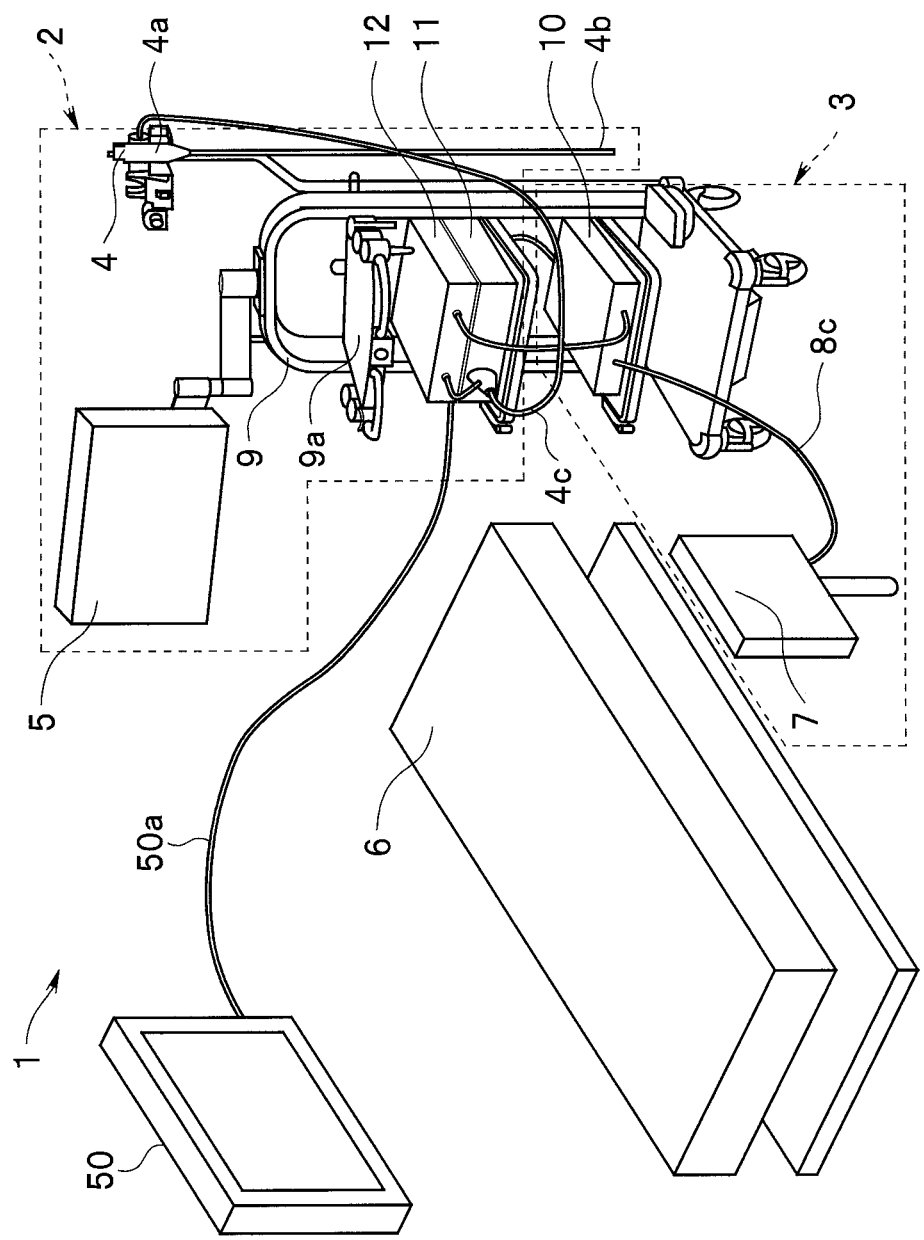
FIG. 2 is a configuration view illustrating an overall configuration of a medical system including the endoscope insertion observation apparatus in FIG. 1.
Figure 3:
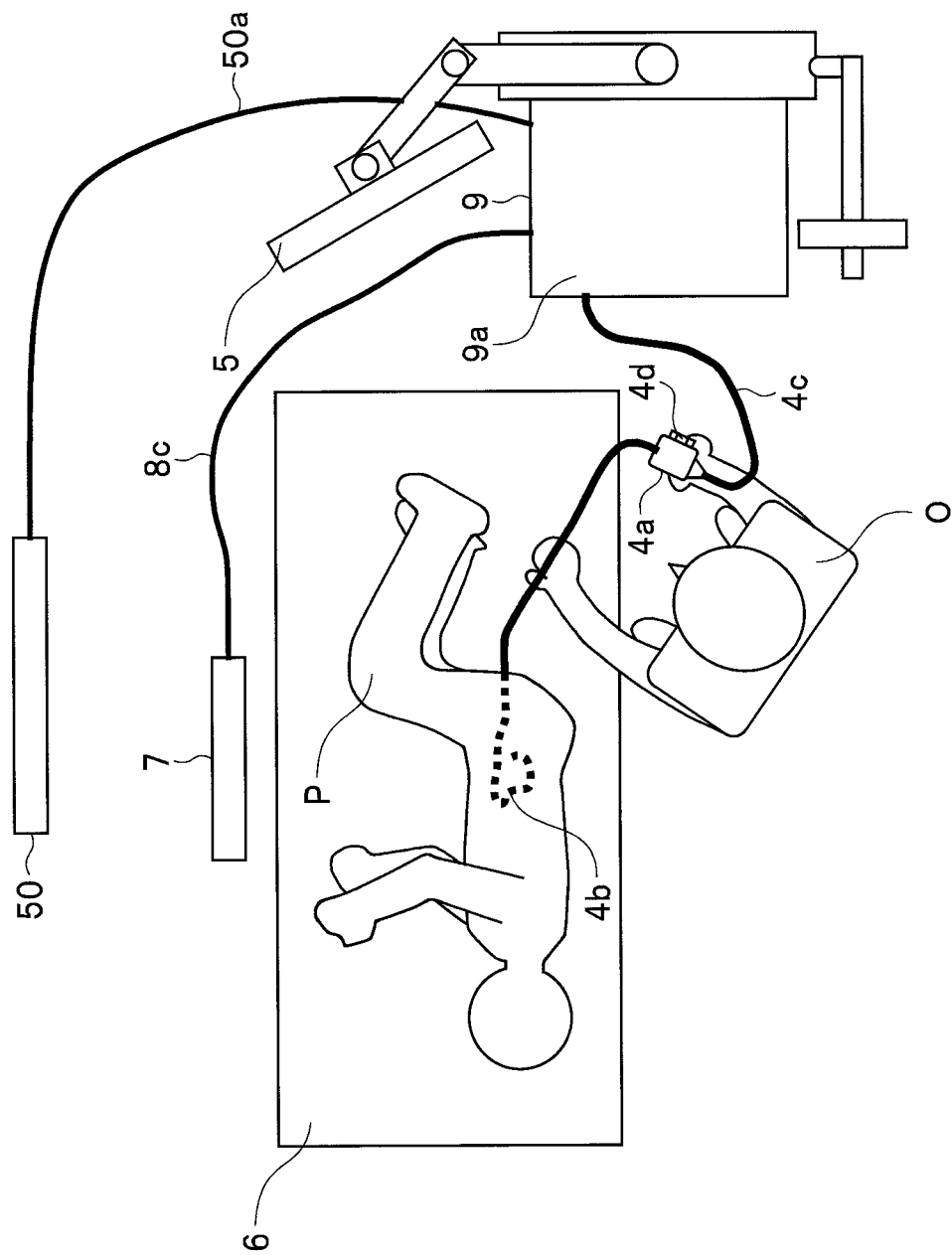
FIG. 3 is an explanatory diagram for describing how to use the endoscope insertion observation apparatus.

FIG. 1 is a block diagram illustrating an endoscope insertion observation apparatus according to an exemplary embodiment. FIG. 2 is a configuration view illustrating an overall configuration of a medical system including the endoscope insertion observation apparatus in FIG. 1. FIG. 3 is an explanatory diagram describing how to use the endoscope insertion observation apparatus.

When an insertion shape image representing an insertion shape of an insertion portion of an endoscope is displayed, a time required for each of procedures may be measured based on an insertion state of the insertion portion of the endoscope and the measured time may be displayed. For example, when taking procedures in a colonoscopy as an example, a time required for an insertion procedure from the insertion of the insertion portion into the anus until the insertion portion reaches the cecum, and a time required for an observation (extraction) procedure during which the insertion portion is extracted from the cecum to the anus are automatically measured and displayed.

In FIGS. 2 and 3, a medical system 1 includes an endoscope apparatus 2 and an endoscope insertion observation apparatus 3. The endoscope apparatus 2 includes an endoscope 4, a light source apparatus 11, a video processor 12, and a monitor 5. The endoscope 4 includes an elongated and flexible insertion portion 4b configured to be inserted into a body cavity of a subject P, an operation portion 4a connected to the proximal end of the insertion portion 4b and including various operation devices, and a cable 4c for connecting the operation portion 4a and the video processor 12.

FIG. 2 illustrates an example in which the light source apparatus 11 and the video processor 12 are placed on a medical trolley 9. In addition, the monitor 5 is attached to a movable arm provided to the medical trolley 9. The endoscope 4 can be latched on a hook of the medical trolley 9.

FIG. 3 illustrates a state where the insertion portion 4b is inserted from the anus into the colon of the subject P lying on a bed 6 for examination. FIG. 3 illustrates a state where an operator O grasps the operation portion 4a and the insertion portion 4b of the endoscope 4 connected to the video processor 12 on the medical trolley 9 by the cable 4c.

The light source apparatus 11 generates illumination light for illuminating the subject. The illumination light from the light source apparatus 11 is guided to a distal end portion of the insertion portion 4b by a light guide inserted into the insertion portion 4b of the endoscope 4, to be applied from the distal end portion of the insertion portion 4b to the subject. An image pickup device, not shown, is disposed at the distal end portion of the insertion portion 4b, and a reflection light (return light) reflected from the subject is image-formed as an object optical image on a light-receiving surface of the image pickup device. The image pickup device is driven and controlled by the video processor 12, and configured to covert the object optical image into an image signal and output the image signal to the video processor 12. The video processor 12 includes an image signal processing section, not shown, and the image signal processing section receives the image signal from the image pickup device, and outputs an endoscopic image subjected to the signal processing to the monitor 5. Thus, as shown in FIG. 1, an endoscopic image 5b of the subject is displayed on a display screen 5a of the monitor 5.

A bending portion is provided at the distal end of the insertion portion 4b, and the bending portion is driven and bent by a bending knob 4d provided on the operation portion 4a. The operator is capable of pushing the insertion portion 4b into the body cavity while operating the bending knob 4d to bend the bending portion.

In the present embodiment, the endoscope insertion observation apparatus 3 for observing the insertion state of the insertion portion 4b includes a control unit 10, a probe 21 for insertion state detection, a receiving antenna 7, and the monitor 50. Note that, as shown in FIG. 3, the monitor 50 is disposed at a position where the operator O who inserts the insertion portion 4b into the subject P can observe the monitor. The control unit 10 of the endoscope insertion observation apparatus 3 is placed on the medical trolley 9, and the probe 21 for insertion state detection is inserted into the insertion portion 4b, as described later. The receiving antenna 7 is connected to the control unit 10 by a cable 8c.

Figure 4:
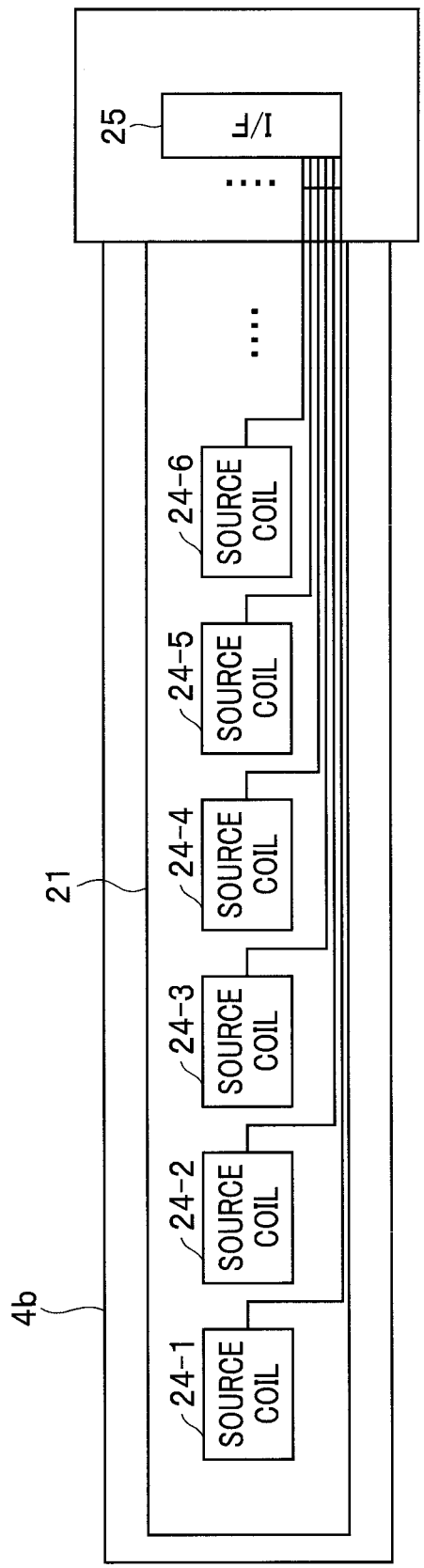
FIG. 4 is a block diagram illustrating an example of a specific configuration of a probe.

FIG. 4 is a block diagram illustrating one example of a specific configuration of the probe 21. As shown in FIG. 4, the probe 21 is inserted into a treatment instrument insertion channel, not shown, in the insertion portion 4b. A plurality of transmission coils 24-1, 24-2, . . . (hereinafter, just referred to as transmission coils 24, when there is no need for discriminating each of the transmission coils) are attached to the probe 21, for example, at a predetermined interval along a probe axis. The probe 21 is inserted into the treatment instrument insertion channel and a distal end or a rear end of the probe 21 is fixed, to thereby allow the plurality of transmission coils 24-1, 24-2, . . . to be disposed at the predetermined interval in the axial direction of the insertion portion 4b.

Note that, in the present embodiment, the transmission coils 24 are incorporated into the insertion portion 4b of the endoscope 4 by inserting the probe 21 into the treatment instrument insertion channel of the endoscope 4 and fixed therein. However, the transmission coils 24 may be directly incorporated into the insertion portion 4b of the endoscope 4.

The receiving antenna 7 includes a plurality of coil blocks, not shown, and disposed on a lateral side of the bed 6, for example. Each of the coil blocks in the receiving antenna 7 is configured by three sense coils wound respectively in three directions such that the coil surfaces of the respective sense coils are orthogonal to one another, and four coil blocks, that is, twelve sense coils are disposed in the receiving antenna 7 as a whole, for example. Each of the sense coils is configured to detect a signal in proportion to a strength of a magnetic field having a component in an axial direction orthogonal to the coil surface of each of the sense coils. For example, each of the coil blocks receives the generated magnetic field and converts the received magnetic field into a voltage signal, to output the voltage signal as a result of detection. The operation states of the probe 21 and the receiving antenna 7 are controlled by the control unit 10.

As shown in FIG. 1, the control unit 10 is provided with a control section 31. The control section 31 can be configured by a processor using a CPU, etc., for example, and may operate based on a program stored in a memory, not shown. The control section 31 controls the entirety of the control unit 10. Note that not only the program in which the processing of the control section 31 is written, but also data to be used in a position calculation to be described later are stored in the memory, not shown.

The control section 31 controls a transmission section 32. The transmission section 32 is configured by an FPGA (field programmable gate array), for example, and controlled by the control section 31, to generate a sine wave signal for driving the probe 21 and output the generated sine wave signal. Note that the transmission section 32 is controlled by the control section 31 and is configured to be capable of supplying the sine wave individually to each of the coils 24 of the probe 21. That is, the control section 31 is capable of controlling to which of the transmission coils 24 of the probe 21 the sine wave is supplied.

Each of the transmission coils 24 is supplied with a high frequency sine wave from the control unit 10 through an I/F 25 (FIG. 4). Each of the transmission coils 24 receives the high-frequency sine wave, to radiate an electromagnetic wave having a magnetic field to the periphery of each of the coils. Note that the control unit 10 is capable of sequentially driving the respective transmission coils 24-1, 24-2, . . . at an appropriate predetermined time interval, i.e., at an interval of several milliseconds, for example. In addition, the control unit 10 is capable of individually designating a timing at which each of the transmission coils 24-1, 24-2, . . . generates a magnetic field.

The receiving antenna 7 receives, by the sense coils, the magnetic fields generated by the transmission coils 24 to convert the received magnetic fields into voltage signals. The receiving antenna 7 feeds the voltage signals, as a result of detection, to a reception section 33 in the control unit 10. The reception section 33 receives the signals from the receiving antenna 7, performs predetermined signal processing such as amplification processing on the received signals, and thereafter outputs the signals subjected to the signal processing to a position calculation section 34.

The position calculation section 34 is configured by a DSP (digital signal processor), for example, and is configured to perform frequency extraction processing (Fourier transform: FFT) on the inputted digital data, separate the inputted digital data into pieces of magnetic field detection information of the frequency components corresponding to the high-frequency sine waves of the respective transmission coils 24, to extract the pieces of magnetic field detection information, and calculate spatial position coordinates of each of the transmission coils 24 provided in the probe 21 based on each digital data of the separated piece of magnetic field detection information. The calculation result of the position coordinates obtained by the position calculation section 34 is supplied to a scope model generation section 35, an insertion position storage section 38, and an insertion length calculation section 39. The scope model generation section 35 connects the position coordinates of the respective transmission coils 24 to generate a linear image as an insertion shape image.

The insertion shape image generated by the scope model generation section 35 is fed to a scope model display section 36. The scope model display section 36 is configured to be capable of generating display data for causing the monitor 50 to display the insertion shape image generated by the scope model generation section 35. The scope model display section 36 causes the monitor 50 to display, on the display screen thereof, the insertion shape image based on the inputted display data. The monitor 50 can be configured by an LCD, for example, and displays, based on the display data, the insertion shape image based on a relative positional relationship between the transmission coils 24 and the receiving antenna 7.

The insertion shape image generated by the scope model generation section 35 is generated by using a coordinate system (hereinafter, referred to as measurement coordinate system), with the position of the antenna 7 as a reference. The scope model display section 36 performs coordinate transformation for causing the insertion shape image to be displayed at a predetermined position on the display screen of the monitor 50. That is, the scope model display section 36 performs coordinate transformation for transforming the measurement coordinate system into the display coordinate system on the inputted display data. The scope model display section 36 performs the coordinate transformation, to thereby enable the insertion shape image to be displayed in a predetermined orientation and a predetermined size at a predetermined position on the display screen of the monitor 50. In addition, the display position, the orientation, and the size of the insertion shape image can be changed by an operation by an operator.

The operation panel 51 is configured to be capable of receiving a user operation by the operator, or the like, and outputting an operation signal based on the user operation to the control section 31. The operator can designate the change of the size of the insertion shape image, and the like, through the operation panel 51. When an instruction for changing the size of the insertion shape image based on the user operation is given from the control section 31, the scope model display section 36 changes the size of the insertion shape image to be displayed on the monitor 50.

In the present embodiment, the control unit 10 is provided with the insertion position storage section 38 configured to store the spatial position coordinates of the transmission coils 24, the spatial position coordinates being outputted from the position calculation section 34. In order to automatically obtain the examination start clock time of the endoscopy, the insertion position storage section 38 is controlled by the control section 31 to store the information on the insertion position of the subject P into which the insertion portion 4b is inserted. In addition, the insertion position information is used also as information for setting which position on the display screen of the monitor 50 the insertion shape image is displayed. For example, in the colonoscopy, information on the position coordinates of the position of the anus of the subject P is used as the insertion position information.

In order to set the insertion position of the subject P, a marker 41 is used, for example. The marker 41 incorporates a transmission coil, not shown, to which a high-frequency sine wave is applied from the transmission section 32. When the high-frequency sine wave is applied to the transmission coil from the transmission section 32, the marker 41 generates a magnetic field. The magnetic field is received by the receiving antenna 7, and the detection result of the receiving antenna 7 is supplied to the position calculation section 34 through the reception section 33. This enables the position calculation section 34 to acquire the position coordinates of the marker 41 in the measurement coordinate system.

The control section 31 controls the transmission sections 32 so as to output the high-frequency sine wave to the marker 41 in a state where the operator disposes the marker 41 in the vicinity of the anus of the subject P, to thereby enable the position coordinates of the position of the anus to be acquired from the position calculation section 34. The position coordinates are supplied to the insertion position storage section 38. The insertion position storage section 38 retains the position coordinates of the position of the anus of the subject P, to output the position coordinates to the insertion length calculation section 39.

Note that when the marker 41 is pasted in the vicinity of the anus of the subject P, the control section 31 controls the transmission section 32 so as to output the high-frequency sine wave to the marker 41 at a predetermined timing, to thereby cause the insertion position storage section 38 to retain the position coordinates of the position of the anus of the subject P (hereinafter, referred to as anus position coordinates) of the predetermined timing. With such a configuration, even in the case where the position of the anus of the subject P changes, the information on the actual position of the anus is fed to the insertion length calculation section 39.

In the present embodiment, the insertion length calculation section 39 receives the position information of the respective transmission coils 24 from the position calculation section 34. The insertion length calculation section 39 that constitutes the insertion state detection section determines that the insertion of the insertion portion 4b into the anus has started when the position coordinates of the transmission coil 24 disposed at the head of the insertion portion 4b substantially coincides with the anus position coordinates. Then, the insertion length calculation section 39 generates an insertion start signal indicating the start of insertion, to output the generated insertion start signal to a measurement time calculation section 43, and outputs the anus position coordinates to the scope model display section 36.

The scope model display section 36 displays the insertion shape image, on the display screen of the monitor 50, with the position of the anus being coincided with a predetermined position (hereinafter, referred to as display reference position) on the display screen. For example, the scope model display section 36 sets the lowermost end portion at the center in the left/right direction on the display screen as the display reference position, and displays the insertion shape image such that the position of the anus is located at the display reference position.

The insertion length calculation section 39 calculates the insertion length of the insertion portion 4b inserted into the body cavity. The part of the insertion portion 4b at which, among the respective transmission coils 24, a transmission coil 24 whose position coordinates detected by the position calculation section 34 corresponds to the anus position coordinates is disposed is located at the anus, which means that, from the position of the above-described transmission coil 24 to the distal end of the insertion portion 4b is inserted into the body cavity. The distances from the distal end of the insertion portion 4b to the positions of the respective transmission coils 24, which are inserted in the insertion portion 4b, are known, and the insertion length calculation section 39 calculates the length from the position of the coil 24 located at the position of the anus to the distal end of the insertion portion 4b as the insertion length. The insertion length calculation section 39 outputs the information on the calculated insertion length to a site reaching determination section 42.

The site reaching determination section 42 is controlled by the control section 31, and is configured to determine that the insertion portion 4b has reached a target site, when the insertion length calculated by the insertion length calculation section 39 is in a predetermined length range, and the site reaching determination section 42 generates a site reaching signal and outputs the generated site reaching signal to the measurement time calculation section 43.

Note that when the insertion length in the state where the insertion portion 4b reaches the target site starts to become shorter by the extraction of the insertion portion 4b, the insertion length calculation section 39 may determine that the observation (extraction) has started, and generate an extraction start signal, to output the generated extraction start signal to the measurement time calculation section 43.

In addition, when the position coordinates of the transmission coil 24 disposed at the head of the insertion portion 4b substantially coincides with the anus position coordinates in the state where the insertion portion 4b is inserted in the body cavity, the insertion length calculation section 39 may generate an extraction end signal indicating the termination of the extraction and output the generated extraction end signal to the measurement time calculation section 43.

Figure 5:
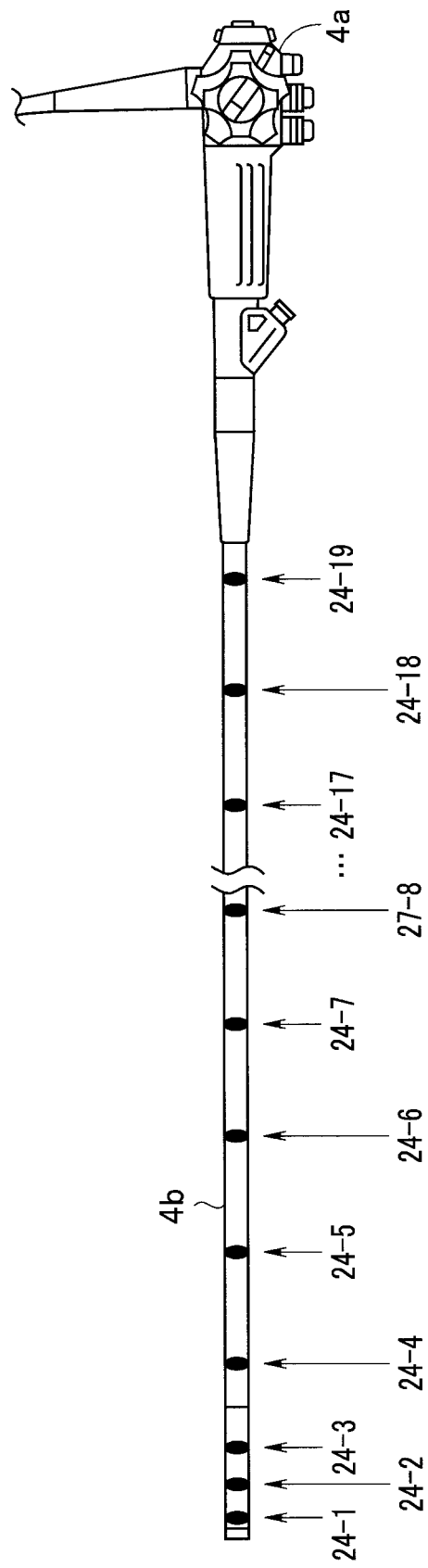
FIG. 5 is an explanatory diagram illustrating exemplary positions of the transmission coils in an insertion portion of an endoscope.
Figure 6:
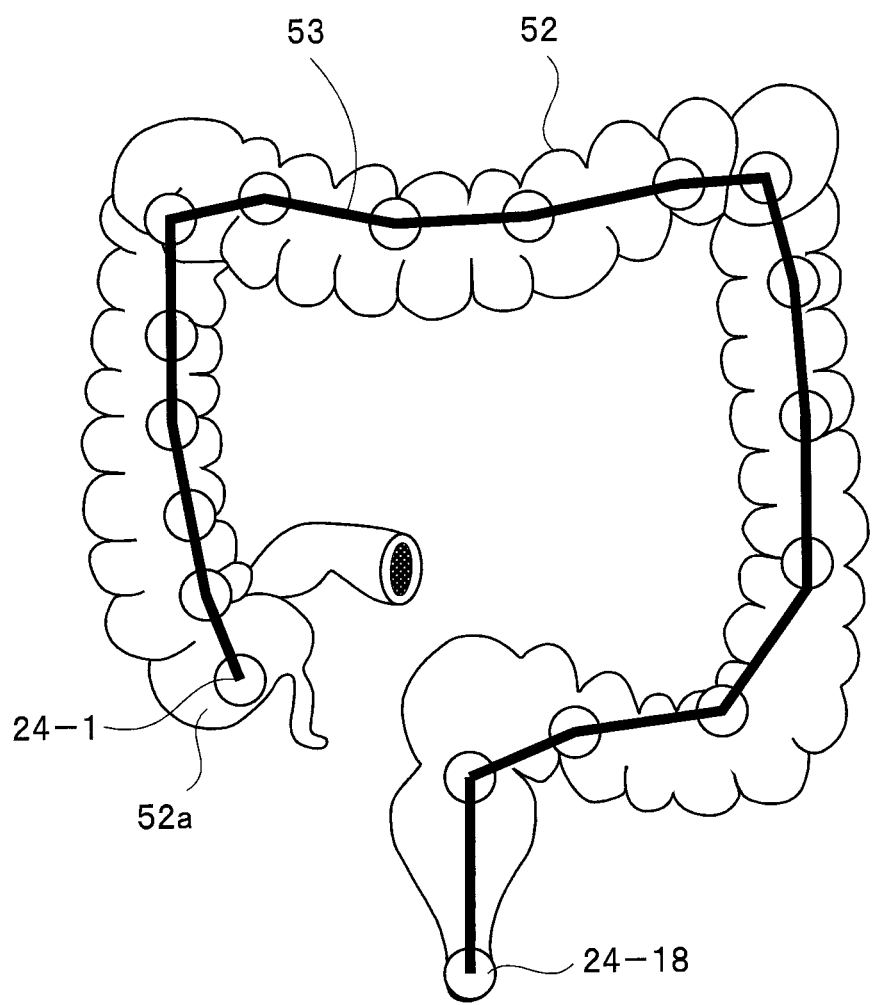
FIG. 6 is an explanatory diagram illustrating positions of transmission coils in a state where the insertion portion is inserted into a colon.

FIG. 5 and FIG. 6 are explanatory diagrams for describing the method for the determination of the target site reaching by the site reaching determination section 42. FIG. 5 illustrates one example of the disposition of the transmission coils 24 in the insertion portion 4b of the endoscope, and FIG. 6 illustrates one example of the positions of the respective transmission coils 24 in the insertion portion 4b inserted into the colon.

In FIG. 5, the disposition positions of the transmission coils 24 in the insertion portion 4b are indicated by the circles. The example shown in FIG. 5 indicates that nineteen transmission coils 24-1 to 24-19 are disposed. The respective disposition positions of the transmission coils 24-1 to 24-19 disposed in the insertion portion 4b of the endoscope are known.

FIG. 6 illustrates the positions of the respective transmission coils 24-1 to 24-18 in the case where the insertion portion 4b is inserted into the colon 52 and the distal end of the insertion portion 4b reaches the cecum 52a. The example in FIG. 6 indicates that the eighteenth transmission coil 24-18 is located at the position of the anus when the transmission coil 24-1 located at the head of the insertion portion 4b reaches the cecum 52a. That is, in the example in FIG. 6, when the length corresponding to the distance from the transmission coil 24-1 to the transmission coil 24-18 is detected as the insertion length by the insertion length calculation section 39, determination can be made that the head of the insertion portion 4b reaches the cecum 52a.

The site reaching determination section 42 determines whether or not the insertion length calculated by the insertion length calculation section 39 reaches the length set as the length from the insertion position to the target site (hereinafter, referred to as target site set length). For example, in the colonoscopy, the site reaching determination section 42 determines whether or not the calculated insertion length reaches the length set as the length from the insertion position to the cecum (hereinafter, referred to as cecum reaching set length). When the insertion length reaches the target site set length, the site reaching determination section 42 determines that the head of the insertion portion 4b has reached the target site and outputs the site reaching signal to the measurement time calculation section 43. For example, in the colonoscopy, when the insertion length reaches the cecum reaching set length, the site reaching determination section 42 outputs the site reaching signal.

The measurement time calculation section 43 is controlled by the control section 31, to calculate the time from the input of the insertion start signal until the input of the site reaching signal as the time required for the insertion procedure, and output the information on the calculated time to the scope model display section 36. In addition, the measurement time calculation section 43 calculates the time from the input of the site reaching signal until the input of the extraction end signal as the time required for the observation (extraction) procedure, and outputs the information on the calculated time to the scope model display section 36.

The scope model display section 36 is configured to be capable of displaying the insertion state display image on the display screen of the monitor 50, the insertion state display image including the insertion shape image and the display indicating the time required for each of the procedures such as the cecum reaching time and the observation (extraction) time.

Note that the control unit 10 includes also a shape detection section 37. The shape detection section 37 is configured to be capable of detecting a predetermined shape of the insertion portion 4b in the body cavity, based on the insertion shape image obtained from the scope model generation section 35. For example, shape patterns such as a loop shape, a stick shape, and the like are stored in the shape detection section 37, and the shape detection section 37 determines whether or not the insertion shape image forms any of the shape patterns, to thereby be capable of detecting that the shape of the insertion portion 4b has which of the shapes such as the linear shape, stick shape, the loop shape, and the like. The shape detection section 37 outputs the information on the detected insertion shape to the scope model display section 36.

The scope model display section 36 is capable of displaying also the information from the shape detection section 37 on the display screen of the monitor 50. For example, when the insertion shape is the loop shape, the scope model display section 36 is capable of displaying, on the display screen, a warning display indicating that the insertion shape is the loop shape.

Note that, in the above description, the position of the anus of the subject P is obtained by using the marker 41. However, if the lying position of subject P on the bed 6 is almost fixed, the position of the anus of the subject P may be considered to be the known position, with the position of the antenna 7 as a reference. In such a case, predetermined anus position coordinates, which are set in advance, may be stored in the insertion position storage section 38.

Figure 7:
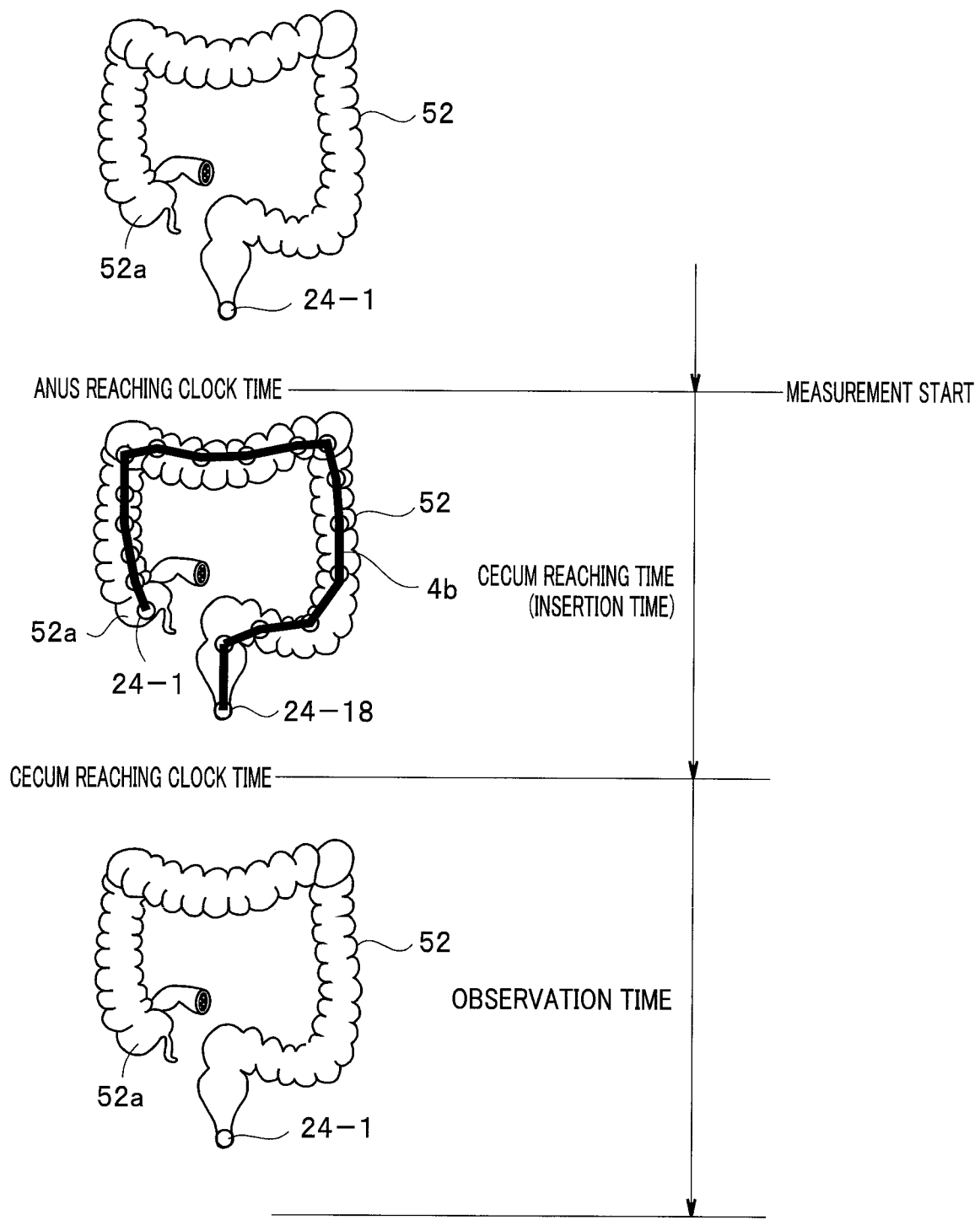
FIG. 7 is an explanatory diagram illustrating a cecum reaching time and an observation time.
Figure 10A:
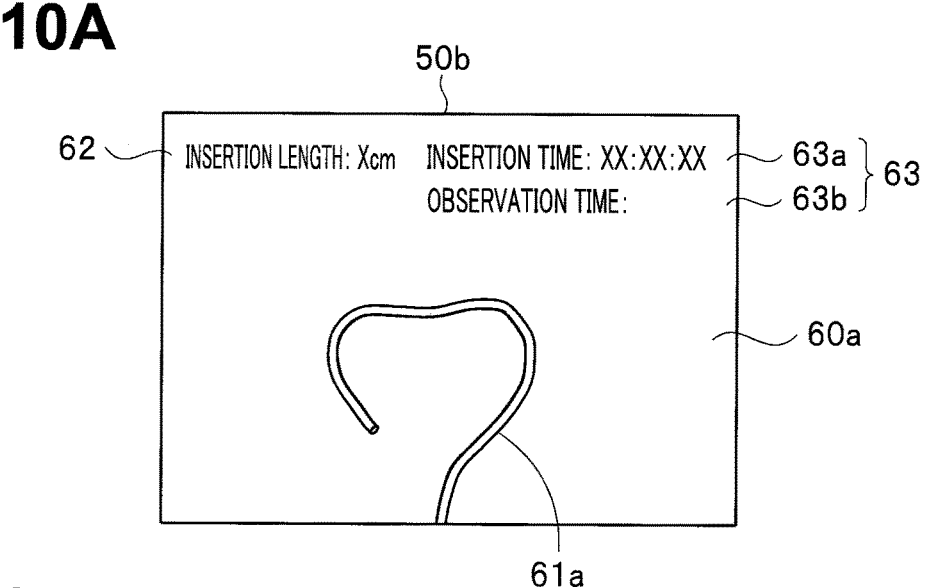
FIG. 10A is an explanatory diagram illustrating an insertion state display image displayed on a display screen of a monitor.
Figure 10B:
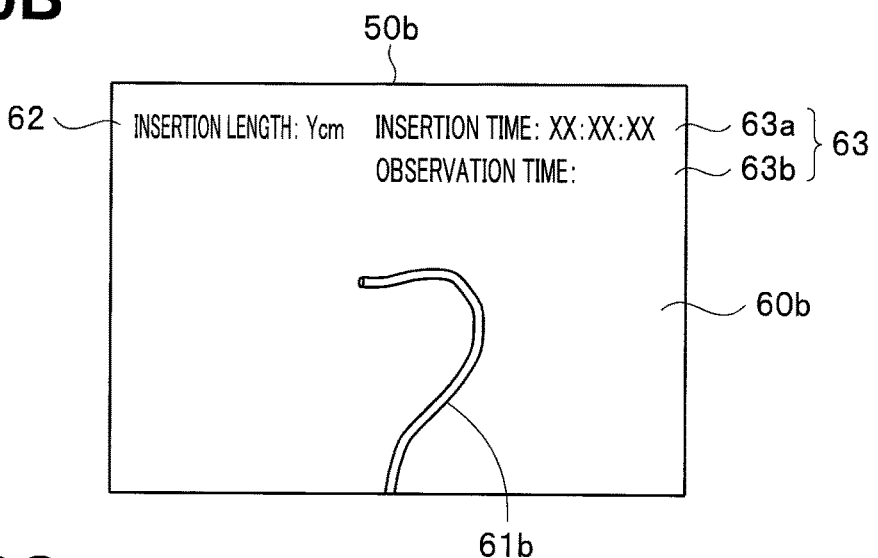
FIG. 10B is an explanatory diagram illustrating an insertion state display image displayed on the display screen of the monitor.
Figure 10C:
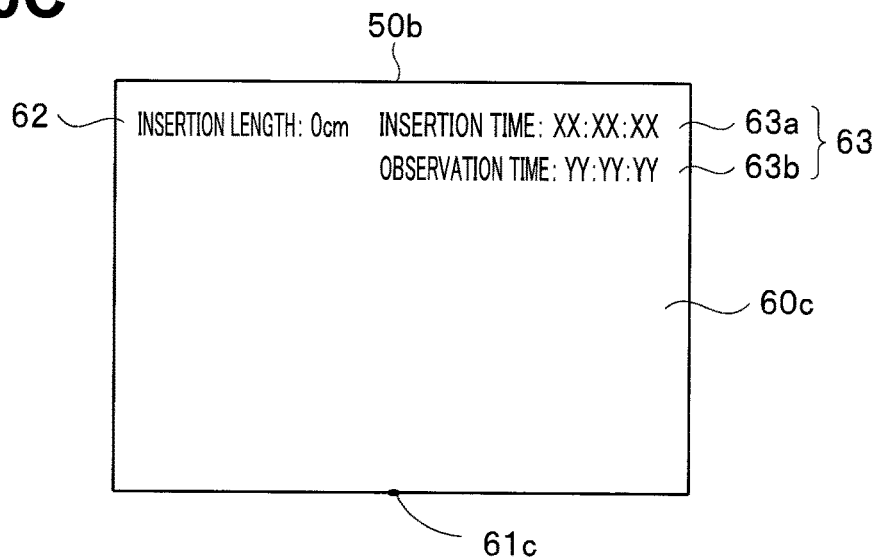
FIG. 10C is an explanatory diagram illustrating an insertion state display image displayed on the display screen of the monitor.

Next, operations in the embodiment thus configured will be described with reference to FIGS. 7 to 10C by taking the procedures in the colonoscopy as an example. FIG. 7 is an explanatory diagram for describing the cecum reaching time and the observation time. Note that the circles in FIG. 7 indicate the positions of the respective transmission coils. FIGS. 8 and 9 are flowcharts for describing the operations. FIG. 8 illustrates a flow for obtaining the cecum reaching time, and FIG. 9 illustrates a flow for obtaining the observation time. FIGS. 10A to 10C are explanatory diagrams illustrating the insertion state display images displayed on the display screen of the monitor 50

In FIG. 7, the lapse of time is shown in the vertical direction. Time measurement is started from the clock time at which the transmission coil 24-1 provided at the distal end of the insertion portion 4b has reached the position of the anus. The measurement time (insertion time) from the measurement start clock time until the clock time at which the transmission coil 24-1 provided at the distal end of the insertion portion 4b reaches the cecum is the cecum reaching time. Furthermore, the measurement time (extraction time) from the clock time of the start of extraction of the insertion portion 4b from the cecum toward the anus side until the clock time at which the transmission coil 24-1 provided at the distal end of the insertion portion 4b reaches the position of the anus is the observation time.

As shown in FIG. 3, it is supposed that the operator inserts the insertion portion 4b into the colon from the anus of the subject P lying in the lateral position on the bed 6 for examination. Prior to the insertion of the insertion portion 4b, the marker 41 is disposed in the vicinity of the anus of the subject P, to obtain the anus position coordinates.

The control section 31 controls the transmission section 32 to apply the high-frequency sine wave to the marker 41. This causes the marker 41 to generate the electromagnetic wave having a magnetic field, and the magnetic field is received by the respective coil blocks in the receiving antenna 7. Then, the detection result corresponding to the strength of the magnetic field is taken from the receiving antenna 7 into the position calculation section 34 through the reception section 33 of the control unit 10.

The position calculation section 34 acquires the anus position coordinates of the marker 41 in the measurement coordinate system from the detection result based on the magnetic field generated by the marker 41, according to the known position estimation algorithm. The anus position coordinates are fed to the insertion position storage section 38 to be retained therein.

In the insertion procedure, the endoscope insertion observation apparatus 3 obtains, at a predetermined time interval, the three-dimensional position coordinates of the plurality of transmission coils 24 in the probe 21 incorporated in the insertion portion 4b. That is, the control section 31 in the control unit 10 controls the transmission section 32 to supply high-frequency signals to the transmission coils 24-1, 24-2, . . . in the probe 21 at respective predetermined timings. The transmission coils 24-1, 24-2, . . . supplied with the high-frequency signals respectively generate electromagnetic waves having magnetic fields. The magnetic fields are received by the respective coil blocks in the receiving antenna 7, and the detection result corresponding to the strength of each of the magnetic fields is taken into the position calculation section 34 through the reception section 33 of the control unit 10.

The position calculation section 34 receives the information on the driving timings of the respective transmission coils 24-1, 24-2, . . . from the control section 31, and obtains the spatial position coordinates of the each of the transmission coils 24-1, 24-2, . . . based on the detection result by each of the coil blocks of the transmission coils 24-1, 24-2, . . . , according to the known position estimation algorithm.

The position coordinates are supplied to the scope model generation section 35, and the scope model generation section 35 generates an insertion shape image based on the position coordinates. The probe 21 is inserted in the treatment instrument insertion channel of the insertion portion 4b, and the respective transmission coils 24 are disposed at the known positions at the predetermined interval along the shape of the insertion portion 4b. That is, the positions of the respective transmission coils 24 indicate discrete positions of the insertion portion 4b. The scope model generation section 35 generates the insertion shape image corresponding to the general shape of the insertion portion 4b by interpolating the discrete positions. Note that the insertion shape image is obtained in the measurement coordinate system.

The scope model generation section 35 feeds the generated insertion shape image to the scope model display section 36. The scope model display section 36 performs coordinate transformation from the measurement coordinate system to the display coordinate system on the insertion shape image received from the scope model generation section 35, to display the insertion shape image subjected to the coordinate transformation on the display screen 50b of the monitor 50.

The position coordinates obtained by the position calculation section 34 is fed also to the insertion length calculation section 39. The insertion length calculation section 39 receives the information on the anus position coordinates as the insertion position information, to start calculation of the length (insertion length) of the insertion portion 4b inserted from the position of the anus into the colon.

In a step S1 in FIG. 8, the insertion length calculation section 39 sets the position of the anus as the position where the insertion length is equal to zero. In a step S2, the measurement time calculation section 43 initializes the cecum reaching time to zero. Next, in a step S3, the insertion length calculation section 39 determines whether or not the calculated insertion length has become larger than zero, that is, whether or not the distal end of the insertion portion 4b is inserted into the anus. When the insertion is started, the insertion length calculation section 39 outputs the insertion start signal to the measurement time calculation section 43. This causes the measurement time calculation section 43 to start the measurement of the cecum reaching time (step S4). Note that the insertion length calculation section 39 may detect that the distal end of the insertion portion 4b has reached the anus (insertion length=0), to generate the insertion start signal.

In a step S5, the insertion length calculation section 39 outputs the calculated insertion length to the measurement time calculation section 43. The measurement time calculation section 43 determines whether or not the calculated insertion length has reached the cecum reaching set length (step S6). When the calculated insertion length has not reached the cecum reaching set length, the measurement time calculation section 43 returns the processing to the step S5, to acquire the insertion length, and repeats the determination of whether or not the insertion length has reached the cecum reaching set length.

When the insertion length has reached the cecum reaching set length, the site reaching determination section 42 generates the site reaching signal and outputs the generated site reaching signal to the measurement time calculation section 43 in a step S7. The measurement time calculation section 43 calculates the time from the input of the insertion start signal until the input of the site reaching signal as the cecum reaching time (step S8). The measurement time calculation section 43 outputs the information on the cecum reaching time as the calculation result to the scope model display section 36. Then, the scope model display section 36 displays, on the display screen of the monitor 50, the insertion state display image including the insertion shape image and the display of the cecum reaching time.

FIG. 10A illustrates an insertion state display image 60a to be displayed on the display screen 50b in this case. In the insertion state display image 60a, an insertion shape image 61a is displayed. Note that, in the insertion state display image 60a in FIG. 10A, the image part of the insertion shape image 61a, which corresponds to the position of the anus, is aligned with the lowermost end position of the display screen 50b.

The insertion state display image 60a includes an insertion length display 62 indicating that the current insertion length is X cm. In addition, the insertion state display image 60a includes a time display 63 indicating the time required for each of the procedures, the time display 63 including an insertion time display 63a indicating the cecum reaching time and an observation time display 63b. In the example in FIG. 10A, the cecum reaching time is XX hours XX minutes and XX seconds.

Next, the operator O observes the respective sites in the colon 52 while extracting the insertion portion 4b from the colon 52. In this case, in a step S11 in FIG. 9, the insertion length calculation section 39 sets, in a memory, not shown, the insertion length in the state at the observation start time point, that is, the state where the distal end of the insertion portion 4b reaches the cecum 52a, as the cecum reaching-time insertion length (insertion length=X). In addition, the measurement time calculation section 43 initializes the observation time to zero in a step S12.

Next, in a step S13, the insertion length calculation section 39 determines whether or not the calculated insertion length has become smaller than X, that is, whether or not the distal end of the insertion portion 4b is started to be extracted from the cecum. When the extraction is started, the insertion length calculation section 39 outputs the extraction start signal to the measurement time calculation section 43. This causes the measurement time calculation section 43 to start the measurement of the observation time (step S14). Note that the insertion length calculation section 39 may generate the site reaching signal and the extraction start signal at the time point at which the distal end of the insertion portion 4b has reached the cecum (insertion length=X).

The insertion length calculation section 39 outputs the calculated insertion length to the measurement time calculation section 43 in a step S15. The measurement time calculation section 43 determines whether or not the calculated insertion length has become equal to or less than zero (step S16). When the insertion length is not equal to or less than zero, the measurement time calculation section 43 returns the processing to the step S15 to acquire the insertion length, and repeats the determination of whether or not the insertion length has become equal to or less than zero.

FIG. 10B illustrates the insertion state display image 60b to be displayed on the display screen 50b at the time. In the insertion state display image 60b, an insertion shape image 61b is displayed. In addition, the insertion state display image 60b includes the insertion length display 62 indicating that the current insertion length is Y cm, and the insertion time display 63a indicating that the cecum reaching time is XX hours, XX minutes, and XX seconds.

When the insertion length becomes equal to or less than zero, the site reaching determination section 42 generates an extraction end signal and outputs the generated extraction end signal to the measurement time calculation section 43 in a step S17. The measurement time calculation section 43 calculates the time from the input of the extraction start signal until the input of the extraction end signal as the observation time (step S18). The measurement time calculation section 43 outputs the information on the observation time, which is the calculation result, to the scope model display section 36. Then, the scope model display section 36 displays, on the display screen 50b of the monitor 50, an insertion state display image including the display of the observation time together with the insertion shape image and the display of the cecum reaching time.

FIG. 10C, illustrates an insertion state display image 60c to be displayed on the display screen 50b at the time. In the insertion state display image 60c, an insertion shape image 61c indicating that the head position of the insertion portion 4b is in the state being extracted from the anus. In addition, the insertion state display image 60c includes the insertion length display 62 indicating that the current insertion length is 0 cm, the insertion time display 63a indicating that the cecum reaching time is XX hours, XX minutes, and XX seconds, and the observation time display 63b indicating that the observation time is YY hours, YY minutes, and YY seconds.

Thus, the present embodiment enables the insertion time required for the insertion procedure, the observation time required for observation (extraction) procedure, and the like to be automatically measured based on the insertion length representing the insertion state of the insertion portion, and to be displayed, for example. There is no need for manual time measurement, which enables the measurement of the time required for each of the procedures to be performed surely and accurately. In addition, the time required for each of the procedures can be displayed together with the insertion shape image, which enables an operator or a medical instructor to easily grasp the progress of insertion state.

Note that, in the above-described embodiment, description has been made on the example in which the cecum is set as the target site and the cecum reaching time and the observation time are calculated. However, it is apparent that the time until the insertion portion reaches the sigmoid colon and the time at which the insertion portion passes through the sigmoid colon may be calculated and displayed.

Figure 11:
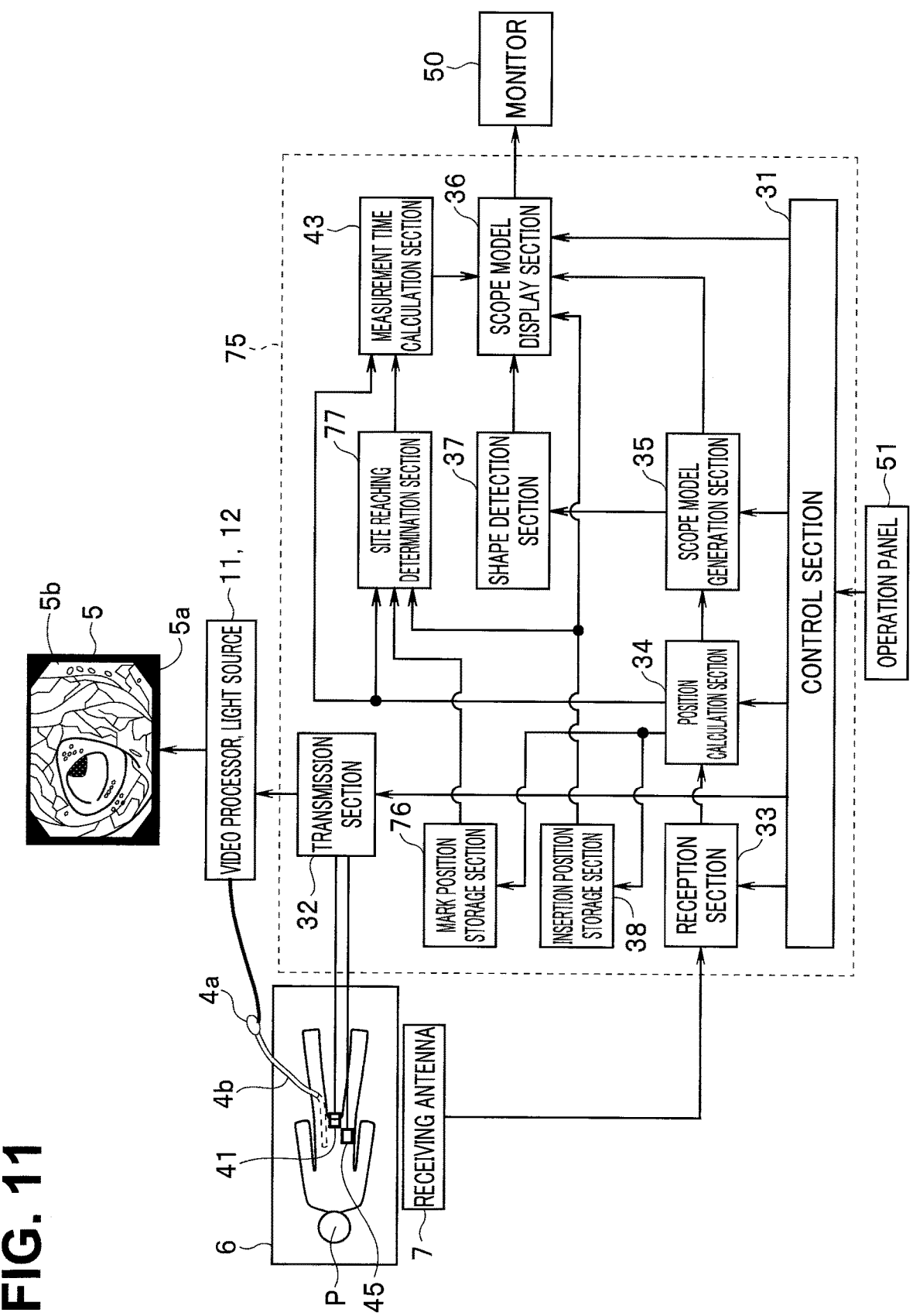
FIG. 11 is a block diagram illustrating an endoscope insertion observation apparatus according to an exemplary embodiment.

FIG. 11 is a block diagram illustrating another exemplary embodiment. In FIG. 11, the constituent elements that are the same as those in FIG. 1 are attached with the same reference signs and descriptions thereof will be omitted. In the above exemplary embodiment, determination of whether or not the distal end of the insertion portion has reached the target site is made based on the insertion length of the insertion portion. The present embodiment uses a marker attached to a position outside the body of a subject that corresponds to the target site of the subject to determine whether or not the insertion portion has reached the target site. Hereinafter, description will be made by taking a colonoscopy in which the target site is cecum as an example. However, any site of the subject may be set as the target site.

A control unit 75 in the present embodiment is different from the control unit 10 in FIG. 1 in that a mark position storage section 76 and a site reaching determination section 77 are employed instead of the insertion length calculation section 39 and the site reaching determination section 42, respectively. In addition, a marker 45 is employed in the present embodiment.

The marker 45 has a configuration similar to that of the marker 41. The marker 45 incorporates a transmission coil, not shown, to which a high-frequency sine wave is applied from the transmission section 32. When receiving the high-frequency sine wave from the transmission section 32, the marker 45 generates a magnetic field. The magnetic field is received by the receiving antenna 7, and the detection result obtained by the receiving antenna 7 is supplied to the position calculation section 34 through the reception section 33. This enables the position calculation section 34 to acquire the spatial position coordinates of the marker 45 in the measurement coordinate system.

The operator estimates the position of the cecum of the subject P from the outside the body of the subject, and fixes the marker 45 to the estimated position by pasting the maker to the estimated position, for example. As a method for estimating the position of the cecum, Mcburney's point can be used, for example. The Mcburney's point is located in the right lower quadrant of the abdomen, and when the line connecting the right anterior superior iliac spine and the umbilicus is trisected, the Mcburney's point is located at the one-third position from the right side of the line. In a diagnosis of appendicitis, the Mcburney's point is widely known as a method for estimating the position of the cecum from the outside the body. The method is used also in the apparatus for palpation training. The control section 31 controls the transmission section 32 to output the high-frequency sine wave to the marker 45 in this state, to thereby enable the position coordinates of the Mcburney's point, i.e., the position coordinates of the position near the cecum to be obtained from the position calculation section 34. The position calculation section 34 supplies the position coordinates to the mark position storage section 76. The mark position storage section 76 stores the position coordinates of the Mcburney's point as a set position coordinates of the cecum (hereinafter, referred to as the cecum set position coordinates), and supplies the cecum set position coordinates to the site reaching determination section 77.

The information on the anus position coordinates is also fed from the insertion position storage section 38 to the site reaching determination section 77. The site reaching determination section 77 receives the position information from the position calculation section 34, and when the position coordinates of the transmission coil 24-1 in the vicinity of the distal end of the insertion portion 4b substantially coincides with the anus position coordinates, the site reaching determination section 77 generates the insertion start signal and outputs the generated insertion start signal to the measurement time calculation section 43. Note that the information on the anus position coordinates from the insertion position storage section 38 is fed also to the scope model display section 36 for specifying the display position of the insertion shape image.

When detecting that the distance between the position coordinates of the transmission coil 24-1 in the vicinity of the distal end of the insertion portion 4b and the cecum set position coordinates is shorter than the arbitrarily set distance (for example, distance of several centimeters from the body surface to the cecum in the standard body size at the time when the body surface is pressed in the palpation), the site reaching determination section 77 generates a site reaching signal and outputs the generated site reaching signal to the measurement time calculation section 43. In addition, when the position coordinates of the transmission coil 24-1 in the vicinity of the distal end of the insertion portion 4b starts to get away from the cecum set position coordinates, the site reaching determination section 77 generates an extraction start signal and outputs the generated extraction start signal to the measurement time calculation section 43. In addition, when the position coordinates of the transmission coil 24-1 in the vicinity of the distal end of the insertion portion 4b substantially coincide with the anus position coordinates after the start of extraction, the site reaching determination section 77 generates an extraction end signal and outputs the generated extraction end signal to the measurement time calculation section 43.

Figure 12:
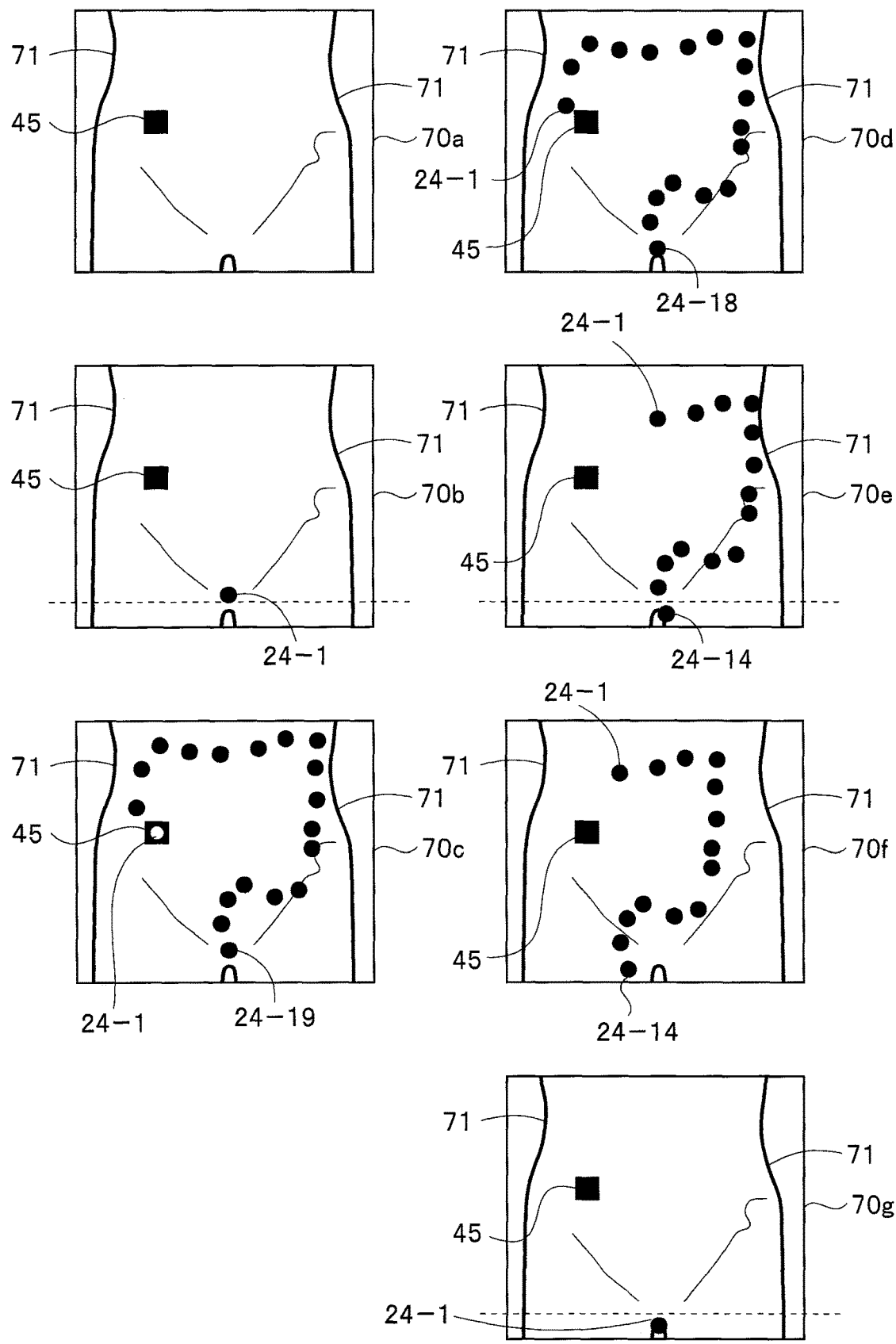
FIG. 12 is an explanatory diagram illustrating an operation in an exemplary embodiment.

Next, operations in the embodiment thus configured will be described with reference to the explanatory diagram in FIG. 12 by taking the procedures in the colonoscopy as an example. In FIG. 12, black circles or white circles indicate the positions of the transmission coils in the insertion portion 4b in the respective states 70a to 70g in the colonoscopy.

Also in the present embodiment, prior to the insertion of the insertion portion 4b, the anus position coordinates are acquired by using the marker 41, and the acquired anus position coordinates are stored in the insertion position storage section 38. In addition, the cecum set position coordinates are stored in the mark position storage section 76 using the marker 45.

FIG. 12 illustrates the position of the marker 45 with respect to an outer shape 71 of the subject P with the black square. The cecum exists in the vicinity of the position of the marker 45 shown with the black square in FIG. 12. The state 70a indicates a state before the insertion of the insertion portion 4b into the subject P. The operator O inserts the insertion portion 4b from the anus of the subject P into the colon. Also in the present embodiment, in the colonoscopy, the position coordinates of the respective transmission coils 24 are obtained by the position calculation section 34.

The position coordinates obtained by the position calculation section 34 are supplied to the site reaching determination section 77. The information on the anus position coordinates is fed, as the insertion position information, to the site reaching determination section 77. The site reaching determination section 77 detects that the insertion portion 4b is inserted from the anus, to generate an insertion start signal and output the generated insertion start signal to the measurement time calculation section 43.

The state 70b in FIG. 12 indicates the position of the coil 24-1 at the timing of the generation of the insertion start signal. The coil 24-1 provided at the head of the insertion portion 4b reaches or passes through the position of the anus, which causes the site reaching determination section 77 to generate the insertion start signal. Note that each of the dashed lines in FIG. 12 illustrates a plane which includes the position of the anus in the case where the patient P lies in parallel to the longitudinal direction of the bed 6, and which is a plane (hereinafter, referred to as insertion position plane) orthogonal to the longitudinal direction of the bed 6. During the normal examination, the patient only changes the direction of the body between the supine position and the lateral position. Therefore, it is supposed that the position of the anus is located within the insertion position plane including the position of the anus detected at the time of the start of the examination. The coil 24-1 reaches or passes through the insertion position plane shown with each of the dashed lines in FIG. 12, to thereby cause the site reaching determination section 77 to generate the insertion start signal or the extraction end signal.

It is supposed that the insertion portion 4b is inserted into the colon and the transmission coil 24-1 provided at the distal end of the insertion portion 4b has reached the position of the cecum in the vicinity of the marker 45. The state 70c in FIG. 12 indicates the positions of the respective coils in this case. The foremost coil 24-1 is located in the vicinity of the position of the marker 45. The cecum set position coordinates are fed from the mark position storage section 76 to the site reaching determination section 77. When detecting that the coil 24-1 has reached the position in the vicinity of the marker 45, the site reaching determination section 77 generates a site reaching signal and outputs the generated site reaching signal to the measurement time calculation section 43.

The measurement time calculation section 43 calculates the time from the input of the insertion start signal until the input of the site reaching signal as the cecum reaching time (insertion time), to output the calculated time to the scope model display section 36. This enables the scope model display section 36 to display the insertion state display image 60a including the insertion shape image 61a and the insertion time display 63a shown in FIG. 10A for example, on the display screen 50b of the monitor 50.

Next, the operator O observes the respective sites in the colon 52 while extracting the insertion portion 4b from the colon 52. The insertion portion 4b is extracted, to thereby cause the foremost coil 24-1, for example, to move to a position away from the vicinity of the position of the marker 45, as shown in the state 70d in FIG. 12. When detecting that the coil 24-1 moves away from the cecum set position coordinates, the site reaching determination section 77 outputs an extraction start signal to the measurement time calculation section 43. This causes the measurement time calculation section 43 to start the measurement of the observation time.

The states 70e, 70f in FIG. 12 show the positions of the respective transmission coils 24 at the time of observation. Both during the insertion and during the extraction, there is a case where the insertion portion 4b moves both in the insertion direction and the extraction direction, and the shape of the colon changes depending on how to insert or extract the insertion portion 4b. The states 70e, 70f show such a change in the positions of the respective coils 24 at the time of observation.

The state 70g in FIG. 12 shows that the transmission coil 24-1 at the distal end of the insertion portion 4b has come out of the anus. When detecting that the transmission coil 24-1 passes through the anus position coordinates, the site reaching determination section 42 generates an extraction end signal and outputs the generated extraction end signal to the measurement time calculation section 43. The measurement time calculation section 43 calculates the time from the input of the extraction start signal until the input of the extraction end signal as the observation time. The measurement time calculation section 43 outputs the information on the observation time, which is a calculation result, to the scope model display section 36. Then, the scope model display section 36 displays, on the display screen of the monitor 50, the insertion state display image including the display of the observation time together with the insertion shape image and the display of the cecum reaching time.

Thus, in the present embodiment, the insertion state of the insertion portion is determined by the comparison between the position of the insertion portion and the marker position designating the target site, and based on the determination result, the insertion time and the observation time required for observation (extraction), etc., can be automatically measured and displayed. Thus, also the present embodiment is capable of obtaining the same effects as those in the above embodiment.

Figure 13:
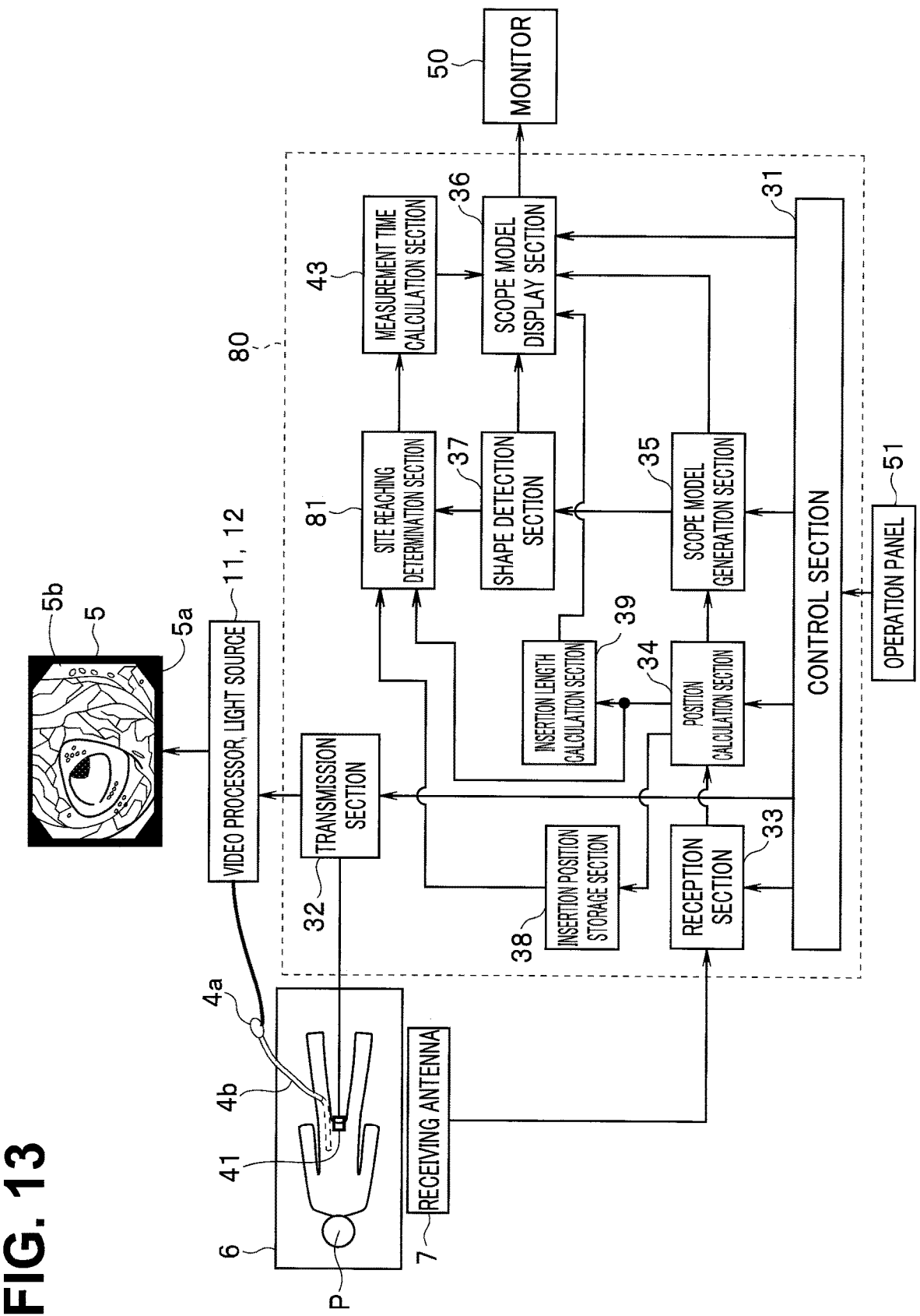
FIG. 13 is a block diagram illustrating an endoscope insertion observation apparatus according to an exemplary embodiment.

FIG. 13 is a block diagram illustrating another exemplary embodiment. In FIG. 13, the same constituent elements as those in FIG. 1 are attached with the same reference signs and descriptions thereof will be omitted. In the present embodiment, the determination of whether the insertion portion has reached the target site is made based on the insertion shape of the insertion portion.

A control unit 80 in the present embodiment is different from the control unit 10 in FIG. 1 in that a site reaching determination section 81 is employed instead of the site reaching determination section 42. In addition to the insertion position information from the insertion position storage section 38 and the position information from the position calculation section 34, the information on the insertion shape from the shape detection section 37 is fed to the site reaching determination section 81. The shape detection section 37 detects, for example, that the insertion shape of the insertion portion 4b is linear shape, and also detects the insertion shape at the time when the insertion portion 4b has reached the target site, to output the information on the insertion shape.

When detecting that the insertion shape at the time when the insertion portion 4b has reached the insertion position becomes a shape at the time of insertion (hereinafter, referred to as insertion-time set shape) such as a linear shape, for example, based on the insertion position information and the position information of the transmission coil 24-1 located at the head position of the insertion portion 4b, the site reaching determination section 81 generates an insertion start signal and outputs the generated insertion start signal to the measurement time calculation section 43. In addition, when detecting that the insertion shape of the insertion portion 4b is the insertion shape in the case where the distal end of the insertion portion 4b reaches the target site (hereinafter, referred to as site reaching set shape), the site reaching determination section 81 generates a site reaching signal and outputs the generated site reaching signal to the measurement time calculation section 43.

For example, the site reaching determination section 81 may be configured to read, from the memory not shown, the information on the site reaching set shape, to compare the number of curved portions and the curvatures of the respective curved portions, which are detected from the insertion shape, with those in the read information on the site reaching set shape, to thereby determine whether or not the insertion portion has reached the target site.

When the insertion shape of the insertion portion 4b starts to change from the site reaching set shape, the site reaching determination section 81 generates an extraction start signal and outputs the generated extraction start signal to the measurement time calculation section 43. In addition, when detecting that the insertion shape in the case where the insertion portion 4b reaches the insertion position has become the shape at the end of the extraction (hereinafter, extraction-time set shape) such as a linear shape, based on the insertion position information and the position information on the transmission coil 24-1 at the head position of the insertion portion 4b, the site reaching determination section 81 generates an extraction end signal and outputs the generated extraction end signal to the measurement time calculation section 43.

Figure 14:
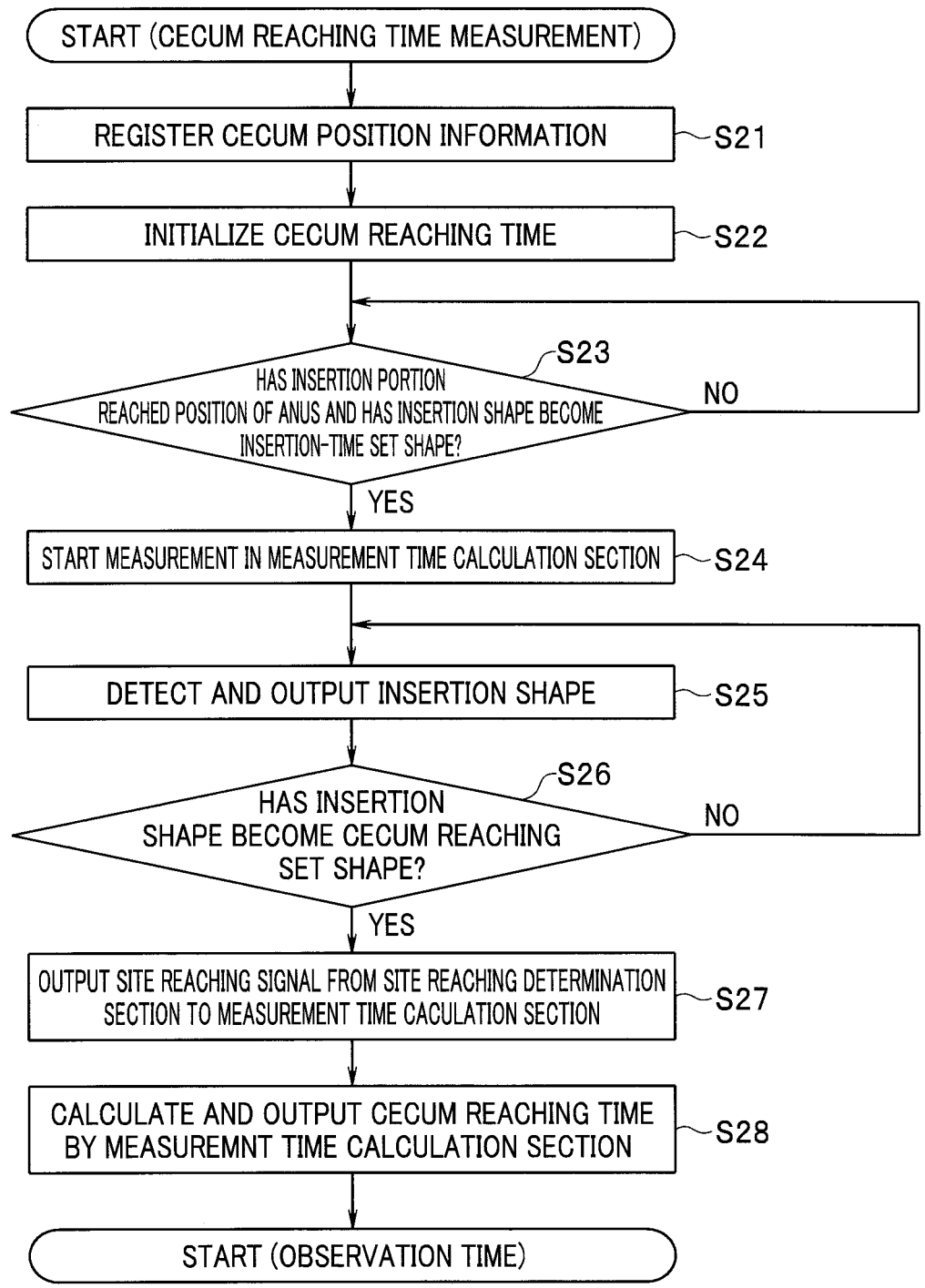
FIG. 14 is a flowchart for measuring the cecum reaching time.
Figure 15:
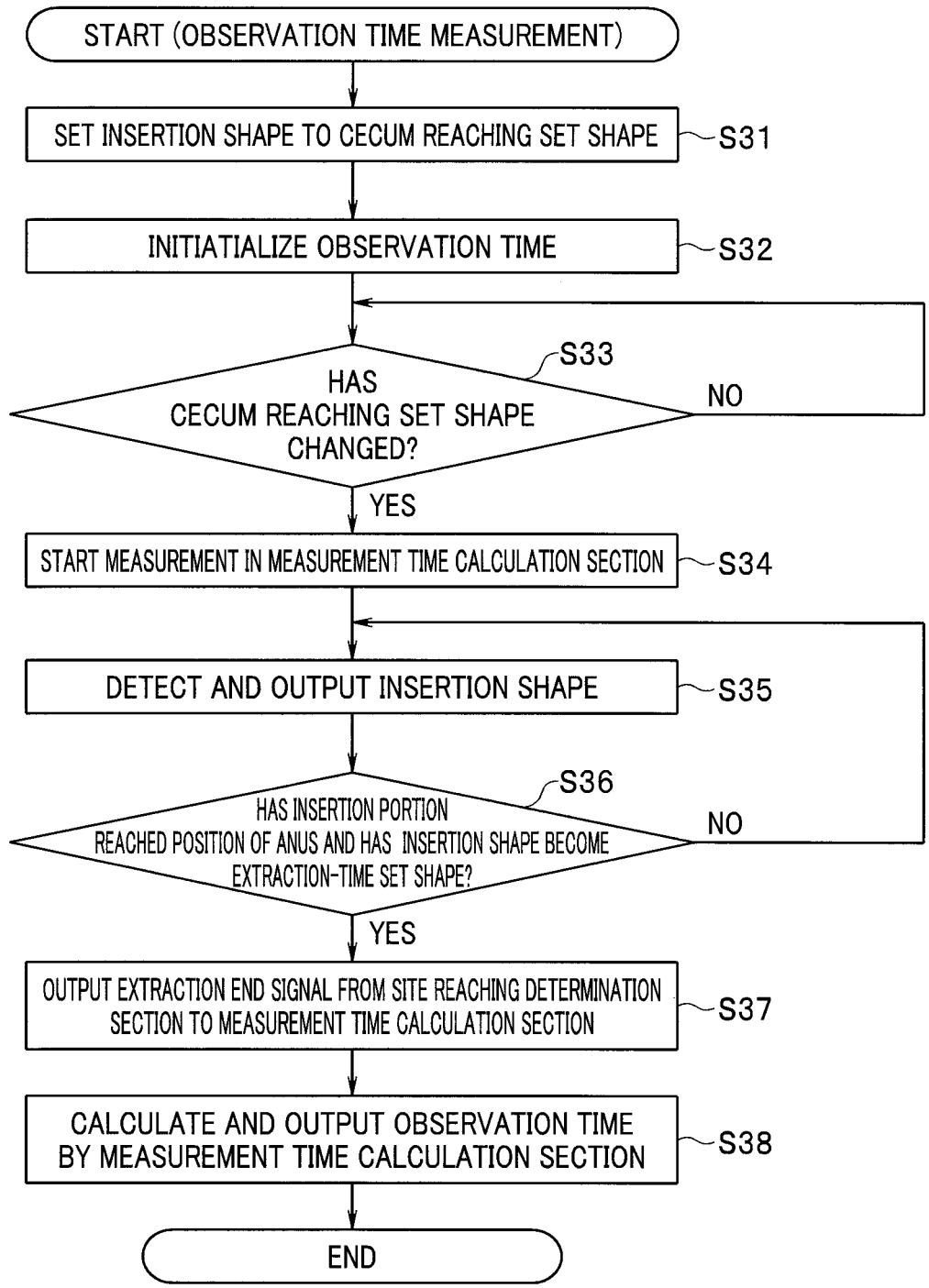
FIG. 15 is a flowchart for measuring the observation time.
Figure 16:
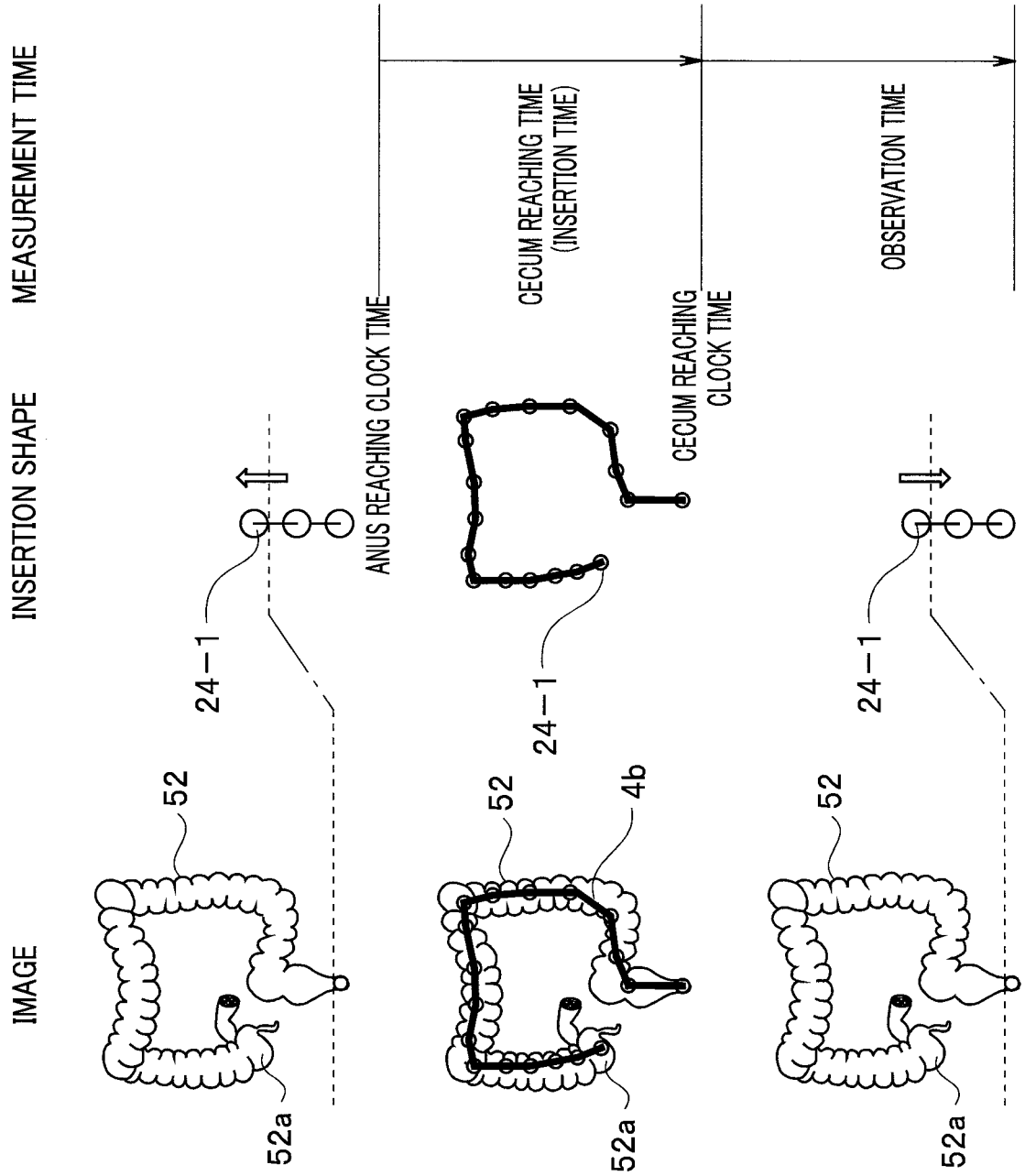
FIG. 16 is an explanatory diagram illustrating a method for obtaining the cecum reaching time and the observation time based on a determination of the insertion shape.

Next, with reference to FIGS. 14 to 16, description will be made on the operations in the present embodiment thus configured by taking the procedures in the colonoscopy as an example. FIG. 14 is a flowchart for measuring the cecum reaching time, and FIG. 15 is a flowchart for measuring the observation time. FIG. 16 is an explanatory diagram for describing a method for obtaining the cecum reaching time and the observation time based on a determination of the insertion shape. Note that the circles in FIG. 16 represent the positions of the respective transmission coils.

In a step S21 in FIG. 14, the anus position information is registered in the insertion position storage section 38. In a step S22, the measurement time calculation section 43 initializes the cecum reaching time to zero. Also in the present embodiment, the position calculation section 34 receives the information on the driving timings of the respective transmission coils 24-1, 24-2, . . . from the control section 31, and obtains the three-dimensional position coordinates of each of the transmission coils 24-1, 24-2, . . . , from the detection result by each of the coil blocks of the transmission coils 24-1, 24-2, . . . , according to the known position estimation algorithm. The position coordinates are supplied to the scope model generation section 35, and the scope model generation section 35 generates an insertion shape image based on the position coordinates. The shape detection section 37 detects various types of insertion shapes in the insertion shape image, and outputs the information on the insertion shapes to the site reaching determination section 81.

In a step S23, the site reaching determination section 81 determines whether or not the distal end of the insertion portion 4b has reached the position of the anus and inserted into the anus, and the insertion shape of the insertion portion 4b has become the insertion-time set shape. The site reaching determination section 81 continues to perform the determination until the insertion shape becomes the insertion-time set shape. The uppermost part in the left section in FIG. 16 illustrates that the distal end of the insertion portion 4b reaches the insertion position plane shown by the dashed line. The uppermost part in the middle section in FIG. 16 illustrates that the transmission coil 24-1 located at the distal end of the insertion portion 4b passes through the insertion position plane, and the insertion shape is the linear shape. In this state, the site reaching determination section 81 determines that the insertion has started, and outputs the insertion start signal to the measurement time calculation section 43. This causes the measurement time calculation section 43 to start the measurement of the cecum reaching time (step S24).

The shape detection section 37 outputs the detection result of the insertion shape to the site reaching determination section 81 (step S25). In a step S26, the site reaching determination section 81 determines whether or not the detected insertion shape has become the cecum reaching set shape which is the site reaching set shape at the time of reaching the cecum (step S26). When the determination result is NO, the site reaching determination section 81 returns the processing to a step S25, to acquire the information on the insertion shape, and repeats the determination of whether or not the insertion shape has become the cecum reaching set shape.

The middle part in the left section in FIG. 16 illustrates that the distal end of the insertion portion 4b reaches the cecum 52a. The shape detection section 37 detects the shape illustrated by the bold line in the middle part in the middle section in FIG. 16. The site reaching determination section 81 makes a similarity determination between the shape illustrated by the bold line and the cecum reaching set shape, i.e., a comparison between the values such as the number of curved portions and the curvatures of the respective curved portions in the shape illustrated by the bold line and the values such as the number of curved portions and the curvatures of the respective curved portions in the cecum reaching set shape, to thereby determine that the distal end of the insertion portion 4b has reached the cecum 52a.

When the insertion shape becomes the cecum reaching set shape, the site reaching determination section 81 generates the site reaching signal and outputs the generated site reaching signal to the measurement time calculation section 43 in a step S27. The measurement time calculation section 43 calculates the time from the input of the insertion start signal until the input of the site reaching signal as the cecum reaching time (step S28). The measurement time calculation section 43 outputs the information on the cecum reaching time, which is the calculation result, to the scope model display section 36. Then, the scope model display section 36 displays, on the display screen of the monitor 50, the insertion state display image including the insertion shape image and the display of the cecum reaching time.

Next, the operator O observes the respective sites in the colon 52 while extracting the insertion portion 4b from the colon 52. In this case, in a step S31 in FIG. 15, the site reaching determination section 81 causes a memory not shown to store the insertion shape at the time of start of the observation, that is, the insertion shape in the state where the distal end of the insertion portion 4b reaches the cecum 52a, as the cecum reaching set shape. Then, the measurement time calculation section 43 initializes the observation time to zero in a step S32.

Next, in a step S33, the site reaching determination section 81 determines whether or not the insertion shape detected by the shape detection section 37 has changed from the cecum reaching set shape, that is, whether or not the distal end of the insertion portion 4b starts to be extracted from the cecum. When the extraction starts, the site reaching determination section 81 outputs the extraction start signal to the measurement time calculation section 43. This causes the measurement time calculation section 43 to start the measurement of the observation time (step S34).

The shape detection section 37 outputs the information on the detected insertion shape to the site reaching determination section 81 in a step S35. The site reaching determination section 81 determines whether or not the distal end of the insertion portion 4b has reached the position of the anus and the detected insertion shape has become the extraction-time set shape (step S36). The lowermost part in the left section in FIG. 16 illustrates that the distal end of the insertion portion 4b reaches the insertion position plane illustrated by the dashed line. The lowermost part in the middle section in FIG. 16 illustrates that the transmission coil 24-1 at the distal end of the insertion portion 4b has passed through the insertion position plane and the insertion shape is a linear shape. In this state, the site reaching determination section 81 determines that the extraction ends, to output the extraction end signal to the measurement time calculation section 43 (step S37). This causes the measurement time calculation section 43 to calculate the time from the input of the extraction start signal until the input of the extraction end signal, as the observation time (step S38).

Other workings are the same as those discussed above with respect to the exemplary embodiment shown in FIGS. 1-10C.

Thus, in the present embodiment, the insertion state of the insertion portion is determined based on the detection result of the insertion shape of the insertion portion, and based on the determination result, the insertion time and the observation time required for the observation (extraction) procedure can be automatically measured and displayed. Also the present embodiment is thus capable of obtaining the same effects as those in the above exemplary embodiments.

Note that reaching to the target site may be determined based on the insertion length and the insertion shape by combining the embodiments.

Figure 17:
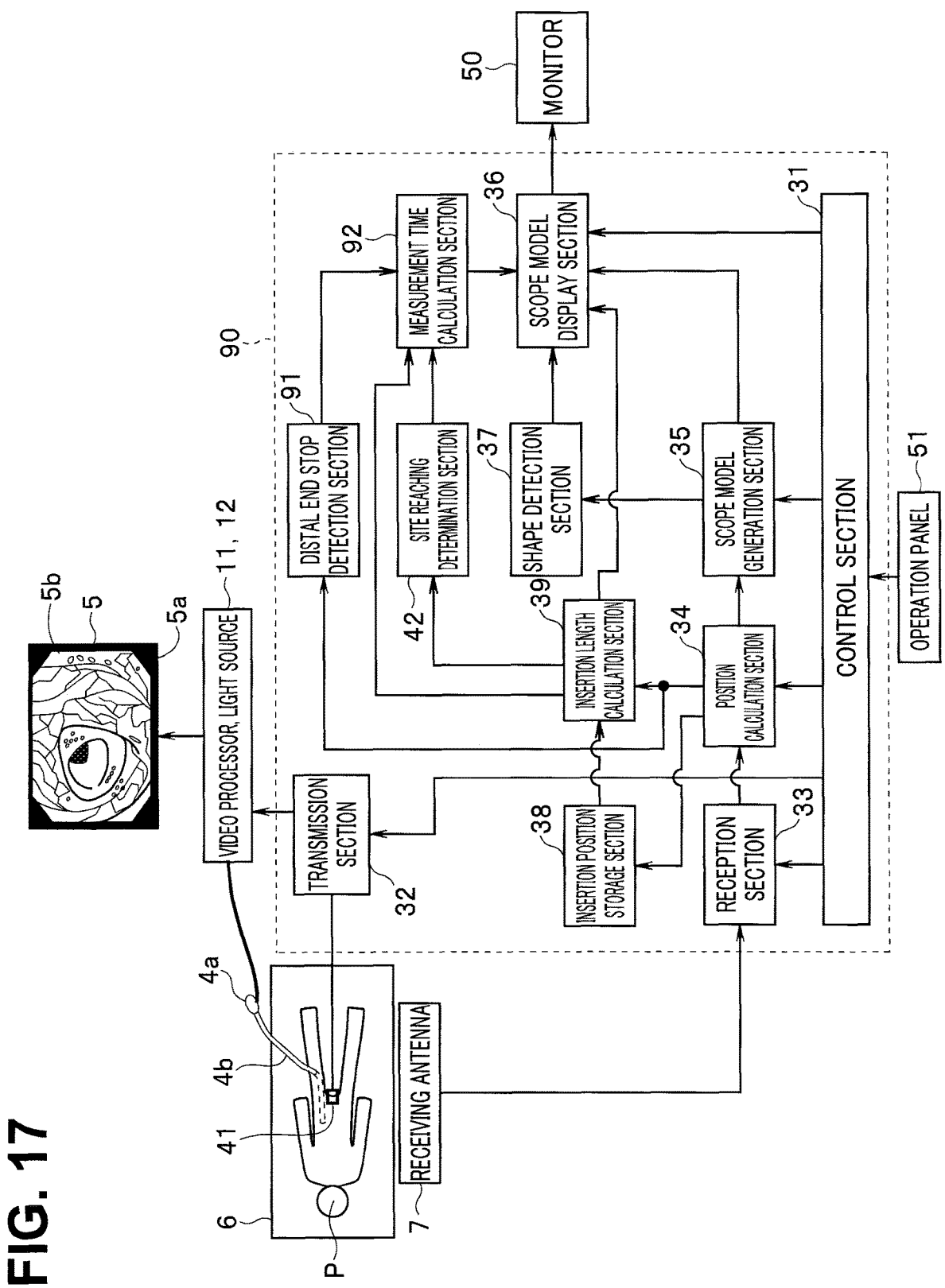
FIG. 17 is a block diagram illustrating an endoscope insertion observation apparatus according to an exemplary embodiment.

FIG. 17 is a block diagram illustrating another exemplary embodiment. In FIG. 17, the same constituent elements as those in FIG. 1 are attached with the same reference signs and descriptions thereof will be omitted. In the above embodiment shown in FIGS. 1-10C, the time from the start until the end of the extraction of the insertion portion is obtained as the observation time. However, in the actual colonoscopy, there is a case where a therapeutic treatment or the like may be performed while extracting the insertion portion, and the observation time obtained in the above embodiment is sometimes different from the time during which the observation is actually performed. Therefore, the present embodiment is intended to be capable of automatically measuring the time during which observation is actually performed.

A control unit 90 in the present embodiment is different from the control unit 10 in FIG. 1 in that a distal end stop detection section 91 is employed and a measurement time calculation section 92 is employed instead of the measurement time calculation section 43. Information on the three-dimensional positions of the respective transmission coils 24 is fed from the position calculation section 34 to the distal end stop detection section 91. The distal end stop detection section 91 determines whether or not the position of the transmission coil 24-1 located in the vicinity of the distal end of the insertion portion 4b is stopped. When the position of the transmission coil 24-1 is stopped, the distal end stop detection section 91 generates a stop signal indicating that the position of the transmission coil 24-1 is stopped and outputs the generated stop signal to the measurement time calculation section 92. When the time during which the stop signal is generated, that is, the time during which the insertion portion 4b is stopped is longer than a predetermined threshold, the measurement time calculation section 92 determines that the time longer than the threshold is time during which treatment such as therapeutic treatment is performed, to cause the memory, not shown, to store the information indicating the time during which the insertion portion is stopped. Note that the measurement time calculation section 92 accumulates, for each input of the stop signal, the time during which determination is made that the insertion portion is stopped for the time longer than the threshold, and causes the memory to store the accumulated time as stopping time.

The measurement time calculation section 92 obtains the observation time by subtracting the stopping time from the time (measurement time) from the input of the extraction start signal until the input of the extraction end signal by the site reaching determination section 42. The measurement time calculation section 92 outputs the information on the calculated observation time to the scope model display section 36.

Figure 18:
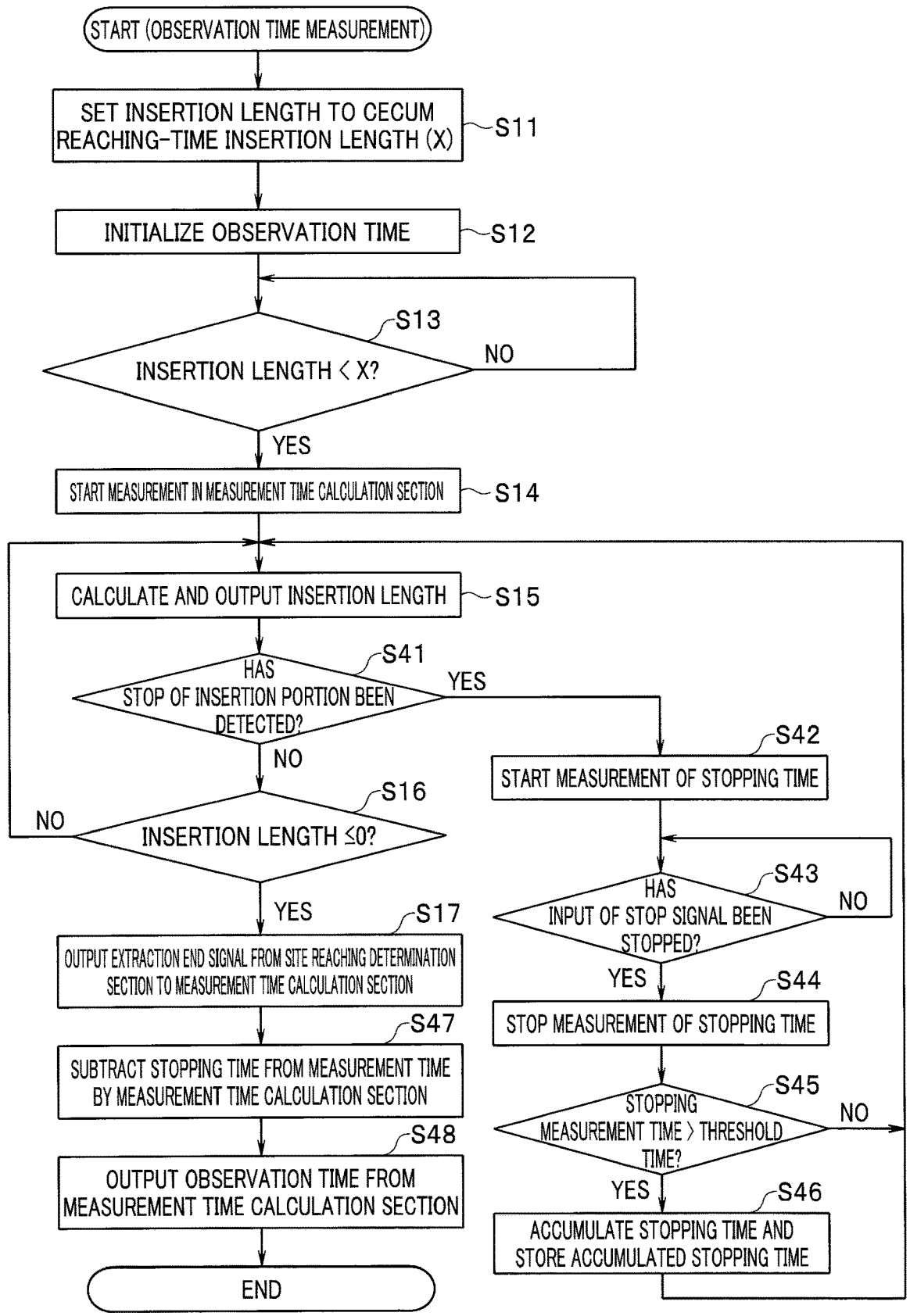
FIG. 18 is a flowchart for measuring the observation time.

Next, operations in the embodiment thus configured will be described with reference to FIGS. 12 and 18 by taking the procedures in the colonoscopy as an example. FIG. 18 is a flowchart for measuring the observation time. In FIG. 18, the same processing steps as those in FIG. 9 are attached with the same reference signs and descriptions thereof will be omitted.

The present embodiment is the same as the above embodiment shown in FIGS. 1-10C in that the site reaching determination section 42 outputs the insertion start signal, the site reaching signal, the extraction start signal, and the extraction end signal, based on the information on the insertion length from the insertion length calculation section 39. In addition, the method for calculating the insertion time in the measurement time calculation section 92 is the same as that in the above embodiment.

In the present embodiment, the procedure from steps S11 to S15 in FIG. 18 are executed for measuring the observation time. Next, in a step S41 in FIG. 18, the distal end stop detection section 91 determines whether or not the position of the transmission coil 24-1 located in the vicinity of the distal end of the insertion portion 4b is stopped. When the insertion portion is not stopped, the processing proceeds from the step S4 to the step S16, and the site reaching determination section 42 determines whether or not the insertion portion 4b has reached the anus. When the distal end of the insertion portion 4b is extracted from the anus, the processing proceeds from the step S16 to the step S17, and the site reaching determination section 42 outputs the extraction end signal to the measurement time calculation section 92.

When detecting that the distal end of the insertion portion 4b is stopped during the time from the start of the extraction until the end of extraction, the distal end stop detection section 91 makes the processing proceed from the step S41 to the step S42, and generates the stop signal to feed the generated stop signal to the measurement time calculation section 92. In response to the generation of the stop signal, the measurement time calculation section 92 starts time measurement. In a step S43, the measurement time calculation section 92 detects whether or not the input of the stop signal is stopped. When the input of the stop signal is stopped, the measurement time calculation section 92 makes the processing proceed from the step S43 to a step S44, to stop the time measurement.

The measurement time calculation section 92 detects whether or not the time during which the stop signal is inputted (stopping measurement time) is longer than the predetermined threshold (step S45). When the stopping measurement time is equal to or shorter than the predetermined threshold, the processing is returned to the step S15. When the stopping measurement time is longer than the predetermined threshold, the measurement time calculation section 92 causes the memory to store the stopping measurement time accumulatively as the stopping time in a step S46. With such a configuration, when the insertion portion 4b is stopped for the time longer than the predetermined threshold time, the total sum of the stopping measurement time is stored in the memory as the stopping time.

When the extraction signal is inputted in the step S17, the measurement time calculation section 92 obtains the observation time by subtracting the stopping time from the measurement time of the extraction (step S47). The measurement time calculation section 92 outputs the information on the observation time calculated in the step S47 to the scope model display section 36 (step S48).

Other workings are the same as those in the above embodiment shown in FIGS. 1-10C.

Thus, the present embodiment is capable of obtaining the same effects as those in the above embodiment. In addition, in the present embodiment, the time calculated by subtracting the stopping time from the time measured in the extraction procedure is obtained as the observation time, to thereby enable the accurate observation time in consideration of the time required for therapeutic treatment and the like to be automatically obtained.

Figure 19:
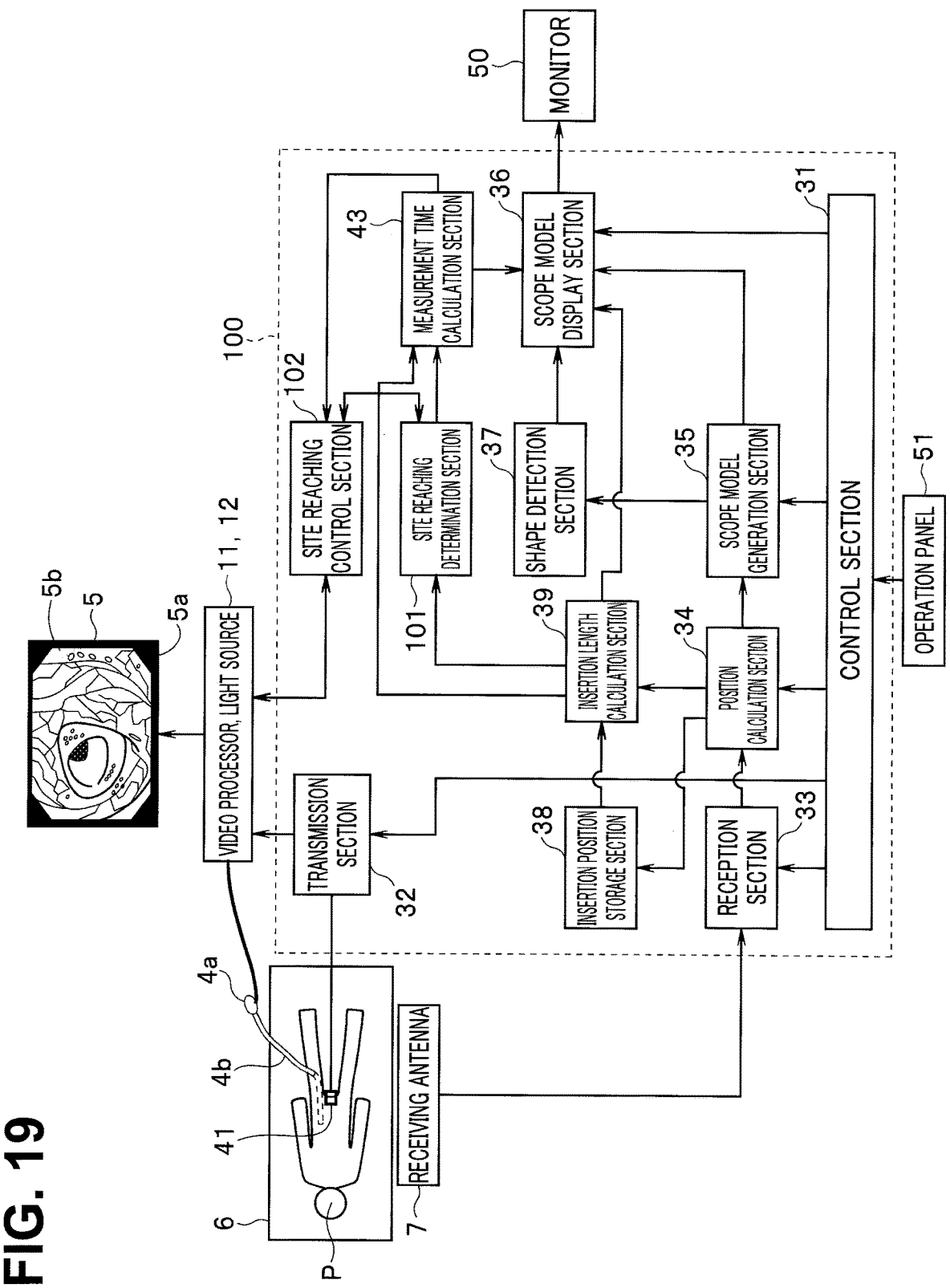
FIG. 19 is a block diagram illustrating an endoscope insertion observation apparatus according to an exemplary embodiment.

FIG. 19 is a block diagram illustrating another exemplary embodiment. In FIG. 19, the same constituent elements as those in FIG. 1 are attached with the same reference signs and descriptions thereof will be omitted. In the above embodiment, description has been made of an example in which the determination of whether or not the distal end of the insertion portion has reached the target site is made based on the insertion length of the insertion portion, and the insertion time is measured based on the determination result. In the present embodiment, external devices to which the target site reaching is instructed by the operation by the operator are also configured to be capable of accurately measuring and displaying the time required for each of the procedures.

A control unit 100 in the present embodiment is different from the control unit 10 in FIG. 1 in that a site reaching control section 102 is employed, and a site reaching determination section 101 is employed instead of the site reaching determination section 42. As with the site reaching determination section 42 in FIG. 1, the site reaching determination section 101 is capable of generating the insertion start signal, the site reaching signal, the extraction start signal, and the extraction end signal, based on the calculation result of the insertion length. The site reaching control section 102 generates an external site-reaching signal indicating that the insertion portion has reached a target site, based on the operation by the operator.

For example, there is a case where the video processor 12 is provided with a time measurement circuit that is capable of measuring the time required for each of the procedures by operation by an operator. For example, the operator refers to the endoscopic image 5b displayed on the display screen 5a of the monitor 5, to thereby confirm that the insertion portion 4b has reached the cecum, for example, as a target site. In this case, the operator performs release operation for photographing an endoscopic image of the cecum, to thereby notify the time measurement circuit in the video processor 12 that the insertion portion has reached the cecum. Then, the time measurement circuit obtains the cecum reaching time and the like and enables the cecum reaching time to be displayed on the display screen 5a.

When receiving a signal generated by such a release operation, the site reaching control section 102 generates an external site-reaching signal, to output the generated external site-reaching signal to the site reaching determination section 101. Note that description has been made on the example in which the site reaching control section 102 generates the external site-reaching signal in response to the release signal. However, the site reaching control section 102 may generate the external site-reaching signal, based on operations of the video processor 12 and the respective operation sections of the operation section 4a or the operation of the operation panel 51, etc.

However, there is a possibility that such an operation by the operator may cause an operational error. There are such cases that the release operation is performed at a timing other than the target site reaching timing, and the release operation is performed when the insertion portion has reached a site other than the target site due to an erroneous judgement by the operator, which has sometimes resulted in a failure in measuring accurate time.

In view of the above, in the present embodiment, when the external site-reaching signal is inputted from the site reaching control section 102 at a timing other than the timing at which determination is made that the insertion portion has reached the target site based on the calculation result of the insertion length, the site reaching determination section 101 outputs to the site reaching control section 102 an alarm signal indicating that the insertion portion does not reach the target site or the insertion portion has passed through the target site at the time of the operation which is a cause of generation of the external site-reaching signal.

When receiving the alarm signal, the site reaching control section 102 transmits the alarm signal to the video processor 12, to cause the time measurement circuit to restart the time measurement. In addition, the information on the time required for each of the procedures, the time being calculated by the measurement time calculation section 43, is fed to the site reaching control section 102. The site reaching control section 102 may transmit the calculation result by the measurement time calculation section 43 to the video processor 12, and perform control to forcibly change the time measurement in the time measurement circuit, using the calculation result by the measurement time calculation section 43.

Furthermore, when receiving the alarm signal, the site reaching control section 102 may cause an alarm indicating that the insertion portion does not reach the target site or the insertion portion has passed through the target site at the time of the operation by the operator to be displayed on the display screen 5a of the monitor 5 and the display screen 50b of the monitor 50.

Figure 20:
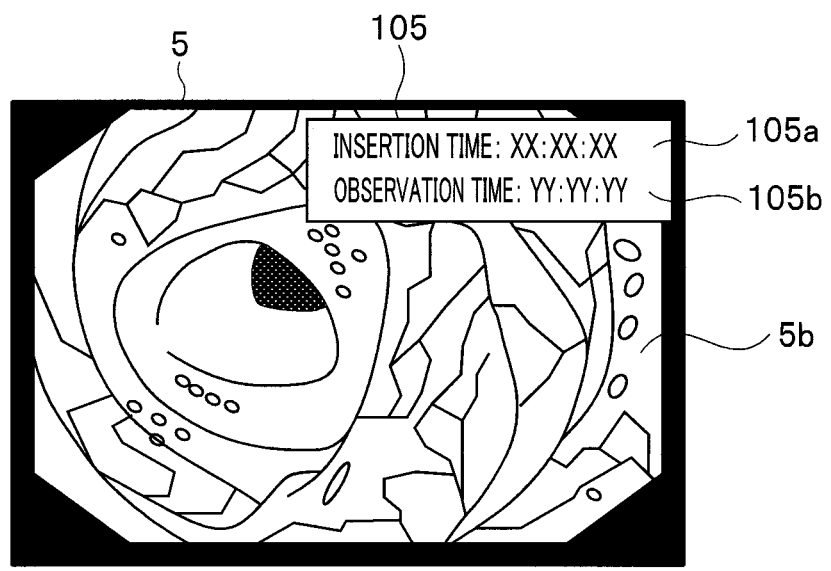
FIG. 20 is an explanatory diagram illustrating an example of a display on a display screen of a monitor.

Next, operations in the embodiment thus configured will be described with reference to FIG. 20 by taking the procedures in the colonoscopy as an example. FIG. 20 is an explanatory diagram illustrating a display example of the display screen of the monitor 5.

The present embodiment is the same as the above embodiment shown in FIGS. 1-10C in that the site reaching determination section 101 outputs the insertion start signal, the site reaching signal, the extraction start signal, and the extraction end signal, based on the information on the insertion length from the insertion length calculation section 39.

In the present embodiment, the external site-reaching signal is outputted from the site reaching control section 102 based on the operation by the operator. In the case where the time measurement circuit is provided in the video processor 12, for example, the time measurement circuit starts the time measurement based on any of the activation of the video processor 12, the completion of the input of the patient information such as the patient's name, and the operation by the operator for instructing the start of the time measurement, and the time measurement circuit obtains the cecum reaching time based on the operation by the operator which indicates that the insertion portion has reached the target site. The video processor 12 is also capable of displaying the cecum reaching time on the display screen 5a of the monitor 5.

FIG. 20 illustrates the display example in the above-described case. In the example shown in FIG. 20, the endoscopic image 5b is displayed on almost the entire screen of the display screen 5a of the monitor 5, and the endoscopic image 5b includes at the upper portion thereof a display region for time display 105 representing the time required for each of the procedures. The time display 105 includes an insertion time display 105a which indicates the cecum reaching time, and the observation time display 105b. Note that, in the stage at which the insertion portion has reached the cecum, the observation time is not displayed in the observation time display 105b.

Now, it is supposed that the external site-reaching signal is outputted from the site reaching control section 102 by the operation based on the operator's erroneous judgement that the insertion portion has reached the cecum, even though the insertion portion 4b does not actually reached the cecum. In this case, the site reaching determination section 101 outputs an alarm signal indicating that the insertion portion 4b does not reach the recur to the site reaching control section 102. The site reaching control section 102 outputs the alarm signal to the time measurement circuit in the video processor 12. Then, the time measurement circuit restarts the measurement of the cecum reaching time and erases the time display of the insertion time display 105a displayed on the display screen 5a of the monitor 5.

Conversely, it is supposed that the external site-reaching signal is not outputted from the site reaching control section 102 based on the operator's erroneous judgement that the insertion portion 4b does not reach the cecum even though the insertion portion 4b has already reached the cecum. In this case, the site reaching determination section 101 outputs the alarm signal indicating that the insertion portion 4b has already reached the cecum to the site reaching control section 102 at the timing of generating the site reaching signal based on the information on the insertion length. The site reaching control section 102 outputs the alarm signal to the time measurement circuit in the video processor 12. Then, the time measurement circuit terminates the measurement of the cecum reaching time, and displays the measurement time at the time of termination of the measurement in the insertion time display 105a on the display screen 5a of the monitor 5.

Note that if the time measurement circuit in the video processor 12 cannot obtain accurate measurement time even if the time measurement circuit receives the alarm signal, the site reaching control section 102 may supply the measurement time from the measurement time calculation section 43, to forcibly change the measurement time by the time measurement circuit to the measurement time from the measurement time calculation section 43.

Other workings are the same as those in the above embodiment shown in FIGS. 1-10C.

The present embodiment is thus capable of obtaining the same effects as those in the above embodiment. In addition, the present embodiment enables the display of the measurement time using the accurate site reaching clock time obtained based on the insertion length even when the measurement time is obtained by designating that the insertion portion has reached the target site by the operation by the operator.

Figure 21:
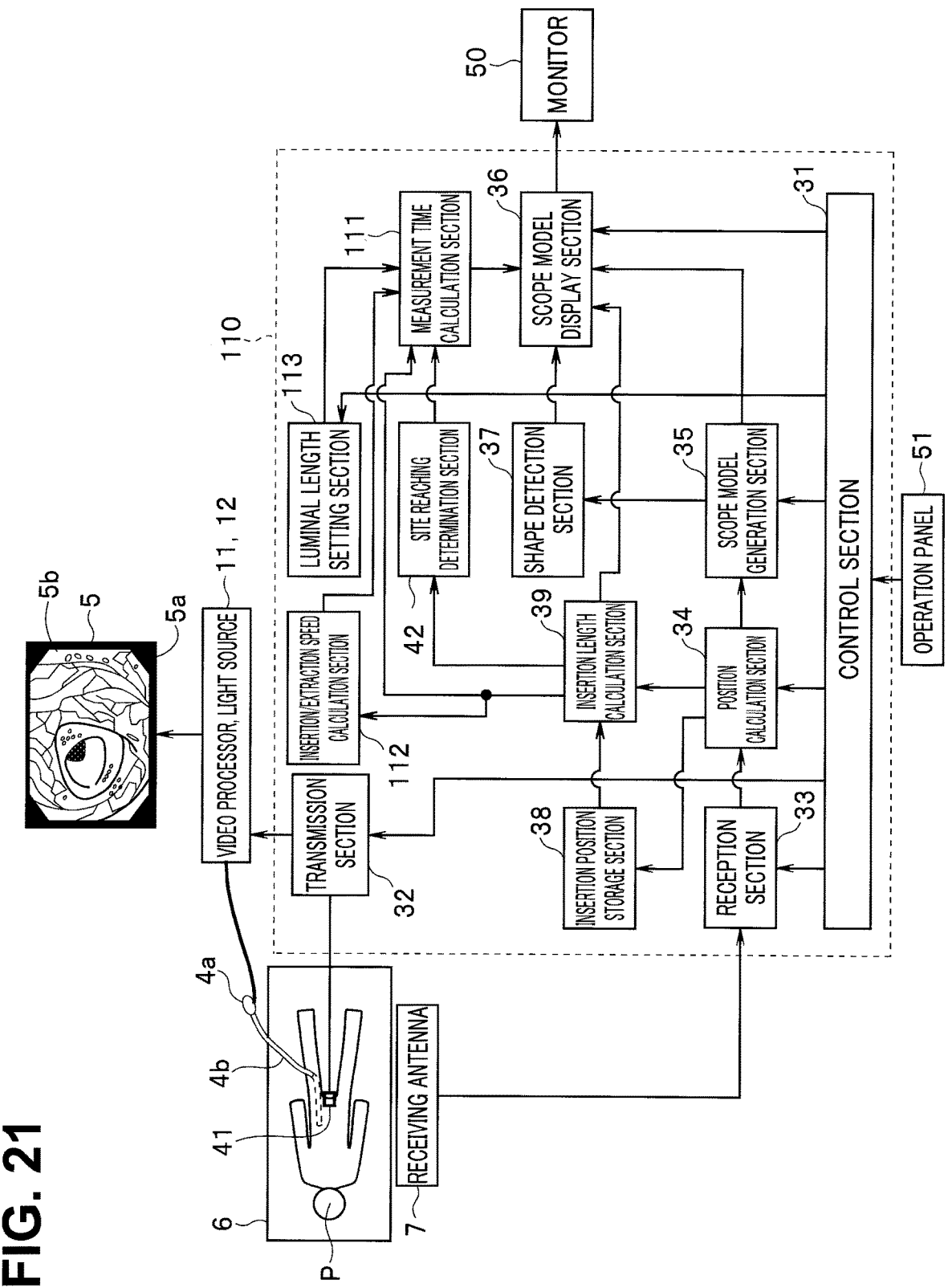
FIG. 21 is a block diagram illustrating an endoscope insertion observation apparatus according to an exemplary embodiment.

FIG. 21 is a block diagram illustrating another exemplary embodiment. In FIG. 21, the same constituent elements as those in FIG. 1 are attached with the same reference signs and descriptions thereof will be omitted. The present embodiment is capable of obtaining and displaying an estimated time until the insertion portion reaches the target site.

A control unit 110 in the present embodiment is different from the control unit 10 in FIG. 1 in that a measurement time calculation section 111 is employed instead of the measurement time calculation section 43, and an insertion/extraction speed calculation section 112 and a luminal length setting section 113 are additionally provided. The information on the three-dimensional positions of the respective transmission coils 24 is supplied from the position calculation section 34 to the insertion/extraction speed calculation section 112. The insertion/extraction speed calculation section 112 calculates a change amount of the insertion length per unit time, that is, the speed of insertion and extraction (hereinafter, referred to as insertion/extraction speed) of the insertion portion 4b. The insertion/extraction speed calculation section 112 outputs information on the calculated insertion/extraction speed to the measurement time calculation section 111.

The luminal length setting section 113 includes a memory, not shown, configured to store a length of the lumen (hereinafter, referred to as luminal length) from the position of the anus to the target site of the subject to be examined into which the insertion portion 4b is inserted. For example, the control section 31 may be configured to be capable of causing the memory in the luminal length setting section 113 to store the information on the luminal length by the operation by the operator on the operation panel 51. The luminal length setting section 113 is configured to, under the control by the control section 31, read the information on the luminal length from the memory and set the read information for the measured time calculation section 111.

As with the measurement time calculation section 43 in FIG. 1, the measurement time calculation section 111 is capable of calculating the insertion time and the observation time, based on the insertion start signal, the site reaching signal, the extraction start signal, and the extraction end signal from the site reaching determination section 42.

Furthermore, in the present embodiment, the measurement time calculation section 111 estimates the time required for the insertion portion 4b to reach the target site from the current position, based on the information on the insertion length, the luminal length, and the insertion/extraction speed. The measurement time calculation section 111 may calculate the estimated time using the following equation (1), for example.

$$\text{Estimated time} = (\text{luminal length} - \text{current insertion length}) / \text{insertion/extraction speed} \quad (1)$$

The measurement time calculation section 111 outputs the information on the calculated estimated time to the scope model display section 36. The scope model display section 36 is configured to be capable of displaying an estimated time display indicating the estimated time on the display screen 50b of the monitor 50.

Figure 22:
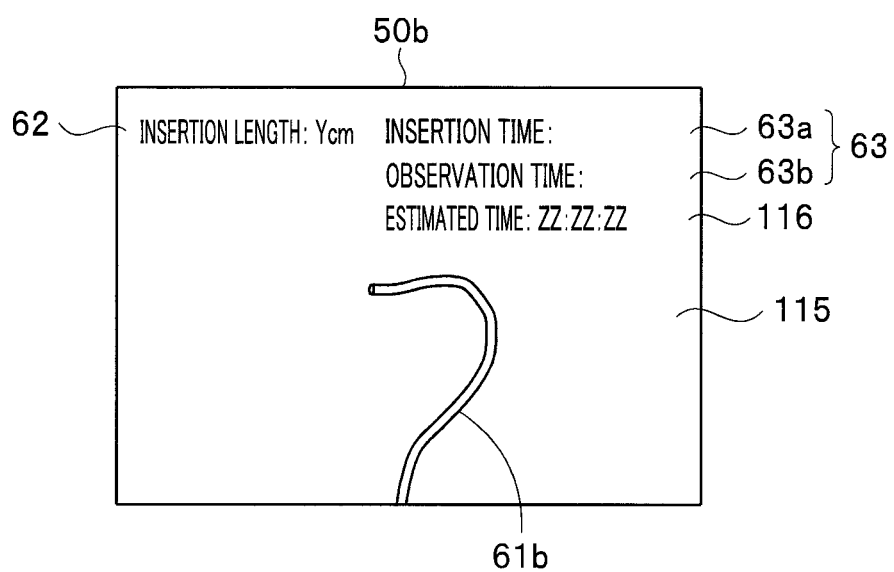
FIG. 22 is an explanatory diagram illustrating an example of a display on a display screen of a monitor.

Next, operations in the embodiment thus configured will be described with reference to FIG. 22 by taking the colonoscopy as an example. FIG. 22 is an explanatory diagram illustrating one example of a display on a display screen of the monitor 50.

The operation that the measurement time calculation section 111 calculates the insertion time and the observation time based on the insertion start signal, the site reaching signal, the extraction start signal, and the extraction end signal from the site reaching determination section 42 is the same as that in the above embodiment shown in FIGS. 1-10C.

That is, the operator inserts the insertion portion 4b from the anus into the colon, to cause the insertion portion 4b to reach the cecum. The position calculation section 34 outputs the information on the three-dimensional positions of the transmission coils 24 in the insertion portion 4b, and the insertion length calculation section 39 calculates the insertion length of the insertion portion 4b using the information on the three-dimensional positions, and outputs the calculated insertion length to the site reaching determination section 42. The site reaching determination section 42 generates the insertion start signal, the site reaching signal, the extraction start signal, and the extraction end signal, based on the calculated insertion length. The measurement time calculation section 111 obtains the cecum reaching time (insertion time) based on the input timing of the insertion start signal and the input timing of the site reaching signal and obtains the observation time based on the input timing of the extraction start signal and the input timing of the extraction end signal.

In the present embodiment, the insertion/extraction speed calculation section 112 calculates the insertion/extraction speed of the insertion portion 4b based on the information on the insertion length from the insertion length calculation section 39 and outputs the calculated insertion/extraction speed to the measurement time calculation section 111. In addition, the luminal length setting section 113 reads the information on the luminal length which is the length of the colon from the anus to the cecum, and outputs the read information to the measurement time calculation section 111.

The measurement time calculation section 111 estimates the time required for the insertion from the current position to the cecum as the target site, based on the information on the insertion length, the luminal length, and the insertion/extraction speed, and outputs the information on the estimated time to the scope model display section 36. The scope model display section 36 displays the estimated time on the display screen 50b of the monitor 5.

FIG. 22 illustrates an insertion state display image 115 to be displayed on the display screen 50b in this case. The insertion shape image 61b is displayed in the insertion state display image 115. In addition, the insertion state display image 115 includes the insertion length display 62 indicating that the current insertion length is Y cm. Furthermore, the insertion state display image 115 includes an estimated time display 116 indicating the estimated time required for the insertion portion to reach the cecum. The example in FIG. 22 indicates that the estimated time to reach the cecum is ZZ hours ZZ minutes, and ZZ seconds.

Thus, the present embodiment is capable of obtaining the same effects as those in the above embodiments, and automatically calculating and displaying the estimated time to reach the target site.

Note that, not only the insertion time and the observation time but also various kinds of estimated time until the insertion portion reaches respective target sites can be calculated as estimated time and displayed.

Figure 23:
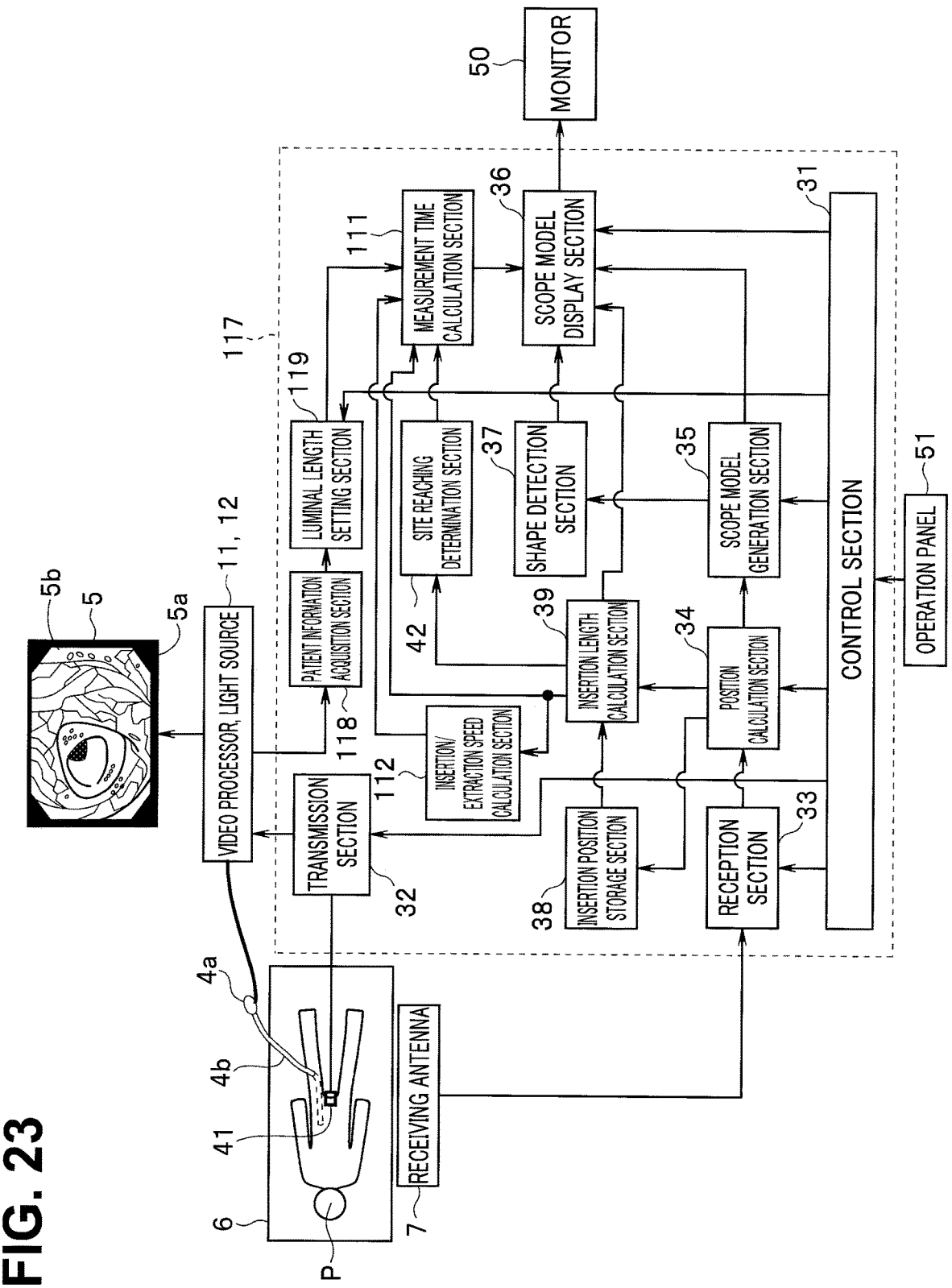
FIG. 23 is a block diagram illustrating an endoscope insertion observation apparatus according to an exemplary embodiment.

FIG. 23 is a block diagram illustrating another exemplary embodiment. In FIG. 23, the same constituent elements as those in FIG. 21 are attached with the same reference signs and descriptions thereof will be omitted. The present embodiment is capable of automatically setting the luminal length based on the patient information.

A control unit 117 in the present embodiment is different from the control unit 110 in FIG. 21 in that a luminal length setting section 119 is employed instead of the luminal length setting section 113, and a patient information acquisition section 118 is additionally provided. The patient information of the patient P to be examined is registered in the video processor 12. The patient information includes patient's ID, patient's name, sex, body height, body weight, BMI (body mass index), and the like.

The patient information acquisition section 118 is configured to receive the patient information from the video processor 12. It is considered that the luminal length differs depending on the size of the subject P. The luminal length setting section 119 obtains the luminal length according to the size of the patient such as the body height, body weight, BMI, and the like of the subject P, to set the obtained luminal length in the measurement time calculation section 111. For example, the luminal length setting section 119 may include a memory configured to store the information on the luminal length corresponding to the size of the subject P, and calculate the luminal length corresponding to the size of the subject P by referring to the memory based on the inputted patient information, to output the calculated luminal length.

Other configurations and workings are the same as those in the above embodiment shown in FIGS. 21 and 22.

Thus, the present embodiment is capable of obtaining the same effects as those in the above embodiment, and setting the luminal length corresponding to the size of the subject P, which provides an advantage of being capable of calculating more accurate estimated time.

Figure 24:
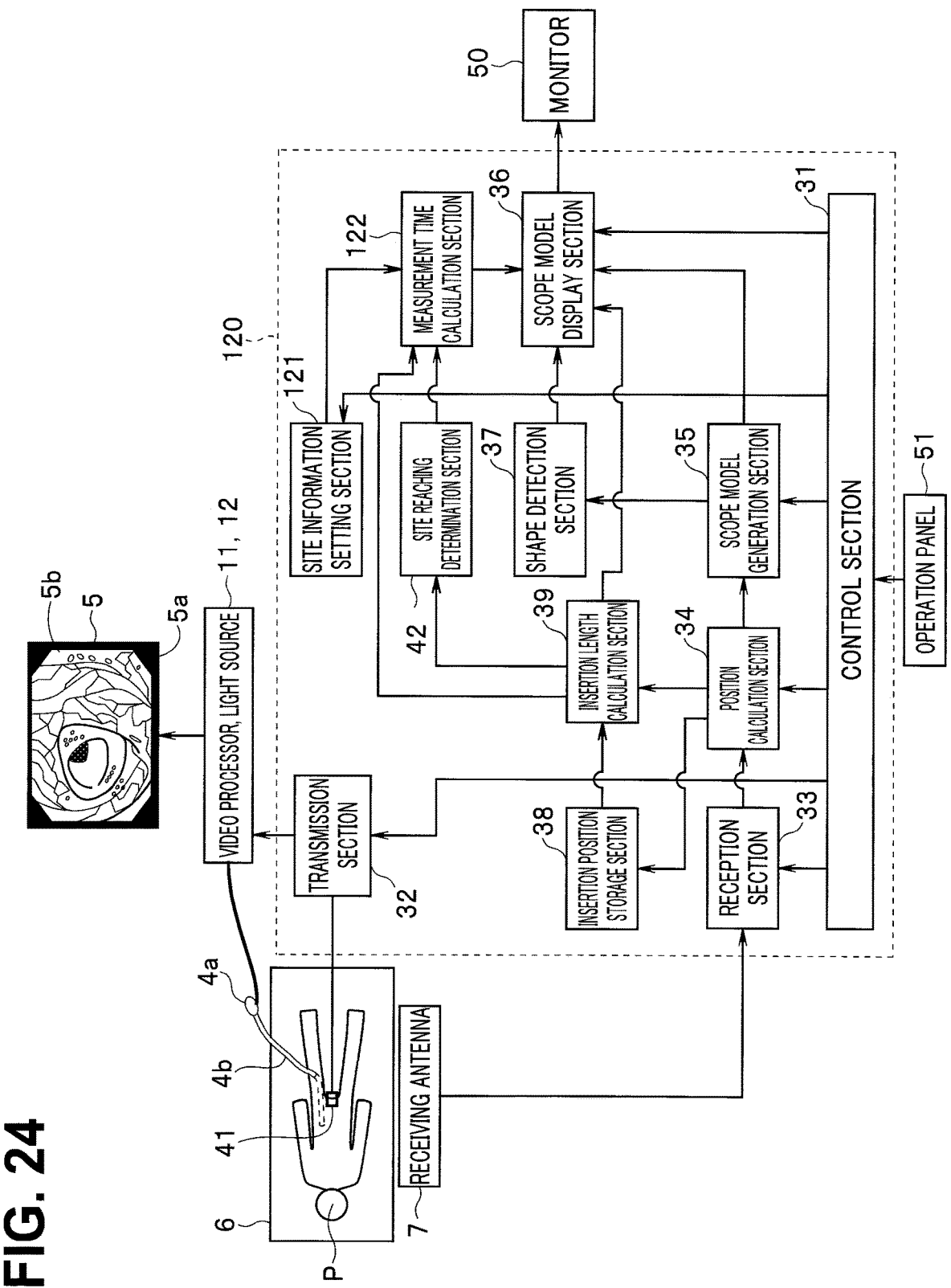
FIG. 24 is a block diagram illustrating an endoscope insertion observation apparatus according to an exemplary embodiment.

FIG. 24 is a block diagram illustrating another exemplary embodiment. In FIG. 24, the same constituent elements as those in FIG. 21 are attached with the same reference signs and descriptions thereof will be omitted. The present embodiment enables automatic calculation of the estimated time to reach the target site by setting, in advance, the standard time required for the movement of the insertion portion between each of the sites in the colon.

A control unit 120 according to the present embodiment is different from the control unit 110 in FIG. 21 in that the insertion/extraction speed calculation section 112 is omitted, and a site information setting section 121 is provided instead of the luminal length setting section 113. The site information setting section 121 includes a memory, not shown, in which the standard time required for the movement of the insertion portion between each of the sites is stored. Note that the control section 31 may be configured to be capable of causing the memory in the site information setting section 121 to store the information on the standard time by the operation by the operator on the operation panel 51, for example.

Figures 25A, 25B:
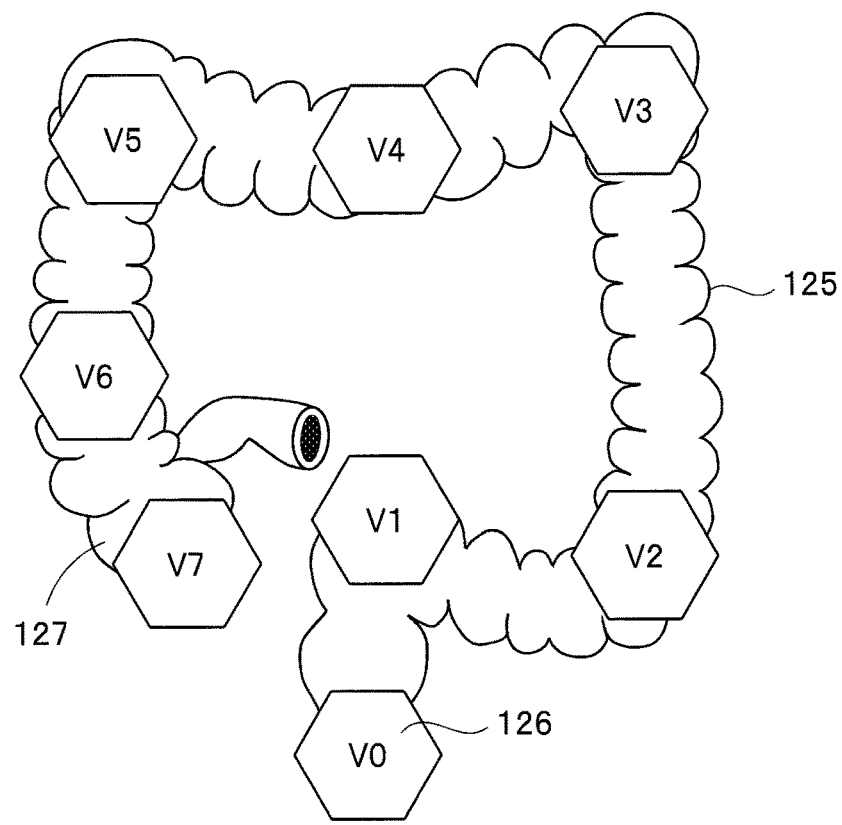
FIG. 25A is an explanatory diagram describing a setting of standard time.
FIG. 25B is an explanatory diagram describing the setting of the standard time.

FIGS. 25A and 25B are explanatory diagrams for describing the setting of the standard time. FIG. 25A illustrates the sites for each of which standard time is set. The example in FIG. 25A illustrates that eight sites V0 to V7 are set in the colon 125. The site V0 is set at the position of the anus 126, and the site V7 is set at the position of the cecum 127. For example, the part between the site V1 and the site V2 is the sigmoid colon.

FIG. 25B shows the standard time set between each of the sites, the standard time being stored in the memory in the site information setting section 121. The example in FIG. 25B shows that the insertion length between the site V0 and the site V1 is 15 cm and the standard time for insertion is set to 10 seconds, and the standard time for extraction is also set to 10 seconds, for example.

Note that not only the standard time (insertion standard time) required for the insertion between each of the sites but also the standard time required for the extraction between each of the sites are set in the site information setting section 121, as shown in FIG. 25B.

As with the measurement time calculation section 111 in FIG. 21, the measurement time calculation section 122 is capable of calculating the insertion time and the observation time, based on the insertion start signal, the site reaching signal, the extraction start signal, and the extraction end signal from the site reaching determination section 42.

Furthermore, in the present embodiment, the measurement time calculation section 122 calculates the time required for the insertion from the start of time measurement until the insertion portion reaches the target site or the time required for the extraction from the target site, as standard estimated time, by adding up the standard time required for the movement of the insertion portion between each of the sites. In addition, every time the measurement time calculation section 122 determines that the insertion portion has reached each of the sites in FIG. 25A based on the information on the insertion length, corrects the standard estimated time between the insertion start position and the target site, based on a difference between the insertion measurement time required for the actual insertion to the site to which the insertion portion has reached and the insertion time obtained from the standard time, or based on a difference between the extraction measurement time required for the actual extraction to the site to which the insertion portion has reached and the extraction time obtained from the standard time, and outputs the corrected standard estimated time to the scope model display section 36, as the estimated time.

Next, operations in the embodiment thus configured will be described by taking the colonoscopy as an example.

The operation that the measurement time calculation section 111 calculates the insertion time and the observation time based on the insertion start signal, the site reaching signal, the extraction start signal, and the extraction end signal from the site reaching determination section 42 is the same as that in the embodiment shown in FIGS. 1-10C.

In the present embodiment, the measurement time calculation section 122 calculates the standard estimated time required for the insertion to the target site or the extraction from the target site, based on the information on the standard time between each of the sites, the standard time being set by the site information setting section 121. Every time the insertion portion reaches each of the sites, the measurement time calculation section 122 calculates the estimated time obtained by correcting the standard estimated time based on the difference between the actual insertion time and the insertion standard time or the difference between the actual extraction end time and the extraction standard time.

It is supposed that the measurement time at the timing at which the insertion portion 4b has reached the site V2 is 32 seconds, for example. In the example in FIG. 25B, the insertion standard time from the start of insertion of the insertion portion 4b until the insertion portion 4b reaches the site V2 is 30 seconds obtained by adding 20 seconds to 10 seconds. Therefore, when the insertion portion 4b has reached the site V2, the measurement time calculation section 122 increases the standard estimated time by adding two seconds to the standard estimated time, to obtain the estimated time.

The measurement time calculation section 122 outputs the information on the estimated time to the scope model display section 36. The scope model display section 36 displays the estimated time on the display screen 50b of the monitor 50 in the similar manner as in FIG. 22, for example.

Other workings are the same as those in the above embodiment shown in FIGS. 21 and 22.

Thus, the present embodiment is capable of obtaining the same effects as those in the above embodiment, and automatically calculating the estimated time to reach the target site by using the standard time required for insertion or extraction between each of the sites, to display the calculated estimated time. The estimated time is obtained by using the standard time between each of the sites, which enables highly accurate estimation.

Figure 26:
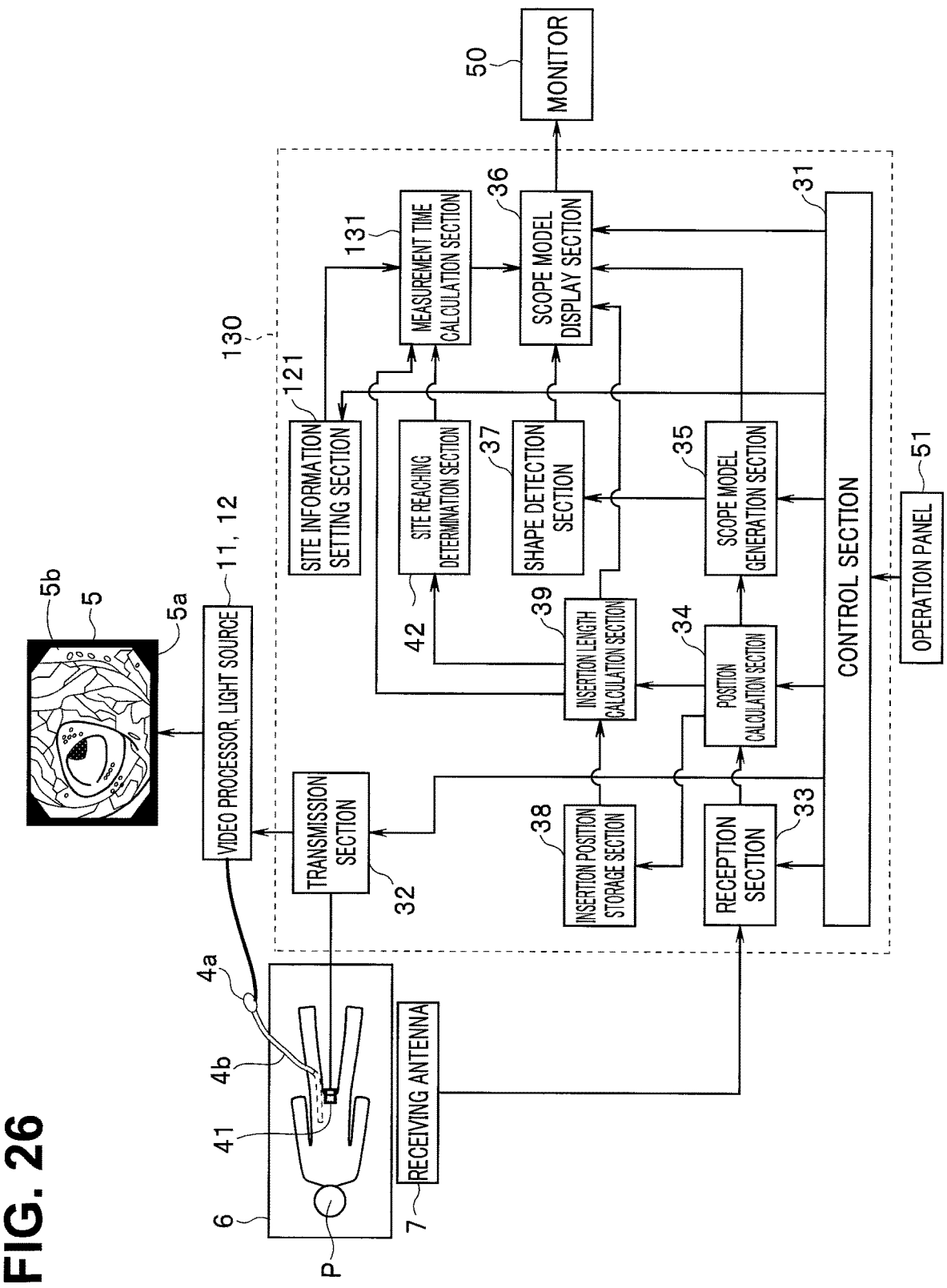
FIG. 26 is a block diagram illustrating an endoscope insertion observation apparatus according to an exemplary embodiment.

FIG. 26 is a block diagram illustrating another exemplary embodiment. In FIG. 26, the same constituent elements as those in FIG. 24 are attached with the same reference signs and descriptions thereof will be omitted. The present embodiment is configured to display a message based on the difference of the actual measurement time with respect to the standard time required for the movement of the insertion portion between each of the sites.

A control unit 130 in the present embodiment is different from the above embodiment shown in FIGS. 24-25B in that a measurement time calculation section 131 is employed instead of the measurement time calculation section 122. As with the measurement time calculation section 122 in FIG. 24, the measurement time calculation section 131 is capable of calculating the insertion time and the observation time based on the insertion start signal, the site reaching signal, the extraction start signal, and the extraction end signal from the site reaching determination section 42. In addition, as with the measurement time calculation section 122 in FIG. 24, the measurement time calculation section 131 is capable of obtaining the standard estimated time based on the information stored in the site information setting section 121, correcting the standard estimated time to reach the target site, based on the difference between the insertion measurement time required for the actual insertion and the insertion time obtained from the standard time or the difference between the extraction measurement time required for the actual extraction and the extraction time obtained from the standard time, and outputting the corrected standard estimated time as the estimated time to the scope model display section 36.

When a difference occurs between the insertion measurement time required for the actual insertion and the insertion time obtained from the standard time or between the extraction measurement time required for the actual extraction and the extraction time obtained from the standard time, the measurement time calculation section 131 according to the present embodiment is capable of displaying a message corresponding to an amount of the difference. For example, when the insertion measurement time or the extraction measurement time, which is required for the insertion portion to reach each of the sites, delays by a predetermined time or longer, with respect to the insertion time or the extraction time, which is obtained from the standard time, or when the insertion measurement time or the extraction measurement time is faster, by a predetermine time or more, with respect to the insertion time or the extraction time obtained from the standard time, the measurement time calculation section 131 is capable of displaying the message indicating the delay or the like on the display screen 50b of the monitor 50.

Figure 27:
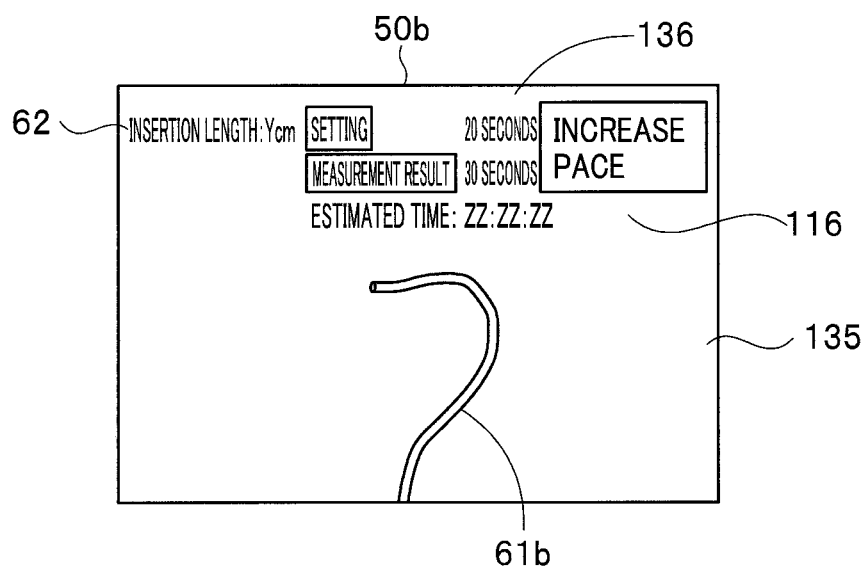
FIG. 27 is an explanatory diagram illustrating a display example on a display screen of a monitor.

Next, operations in the embodiment thus configured will be described with reference to FIG. 27 by taking the colonoscopy as an example. FIG. 27 is an explanatory diagram illustrating a display example on the display screen of the monitor 50.

The operation that the measurement time calculation section 131 calculates the insertion time and the observation time based on the insertion start signal, the site reaching signal, the extraction start signal, and the extraction end signal from the site reaching determination section 42 and the operation that the measurement time calculation section 131 calculates the estimated time using the standard time between each of the sites are the same as those in the embodiment shown in FIGS. 24-25B.

In the present embodiment, when a difference occurs between the insertion measurement time required for the actual insertion and the insertion time obtained from the standard time or between the extraction measurement time required for the actual extraction and the extraction time obtained from the standard time, the measurement time calculation section 131 generates a message corresponding to the amount of the difference and outputs the generated message to the scope model display section 36.

FIG. 27 illustrates a display example in this case. As shown in FIG. 27, an insertion state display image 135 is displayed on the display screen 50b. The insertion shape image 61b is displayed in the insertion state display image 135. In addition, in the insertion state display image 135, the insertion length display 62 indicating that the current insertion length is Y cm and the estimated time display 116 indicating the estimated time to reach the cecum are displayed.

FIG. 27 illustrates a display example of a message display 136 in the case where the distal end of the insertion portion 4b has passed through the site V2 in FIG. 25A, for example. The message display 136 indicates that the standard time (set) required for the movement of the insertion portion from the site V1 to the site V2 is 20 seconds, and the time required for the actual movement (measurement result) is 30 seconds. During the insertion, if the measurement time is longer than the standard time by more than a predetermined threshold time (for example, 0 seconds), the measurement time calculation section 131 causes the message to be displayed. The example in FIG. 27 shows that a notification message "Please increase a pace" in the message display 136, to cause the operator to increase the insertion speed of the insertion portion 4b during the insertion. Such message enables the operator to recognize that the insertion is not performed smoothly.

Note that, during the insertion of the insertion portion 4b, the measurement time calculation section 131 causes the notification message to be displayed when the measurement time is longer than the standard time by more than the predetermined threshold time. On the other hand, during the extraction of the insertion portion 4b, the measurement time calculation section 131 causes the notification message to be displayed when the measurement time is shorter than the standard time by more than predetermined threshold time. The notification message enables the operator to recognize that the operator does not take sufficient time for observation.

The present embodiment is thus capable of obtaining the same effects as those in the above embodiment shown in FIGS. 24-25B, and enabling the operator to easily recognize that the insertion measurement time or the extraction measurement time is longer or shorter than the standard time, to thereby enable effective support for the examination.

Figure 28:
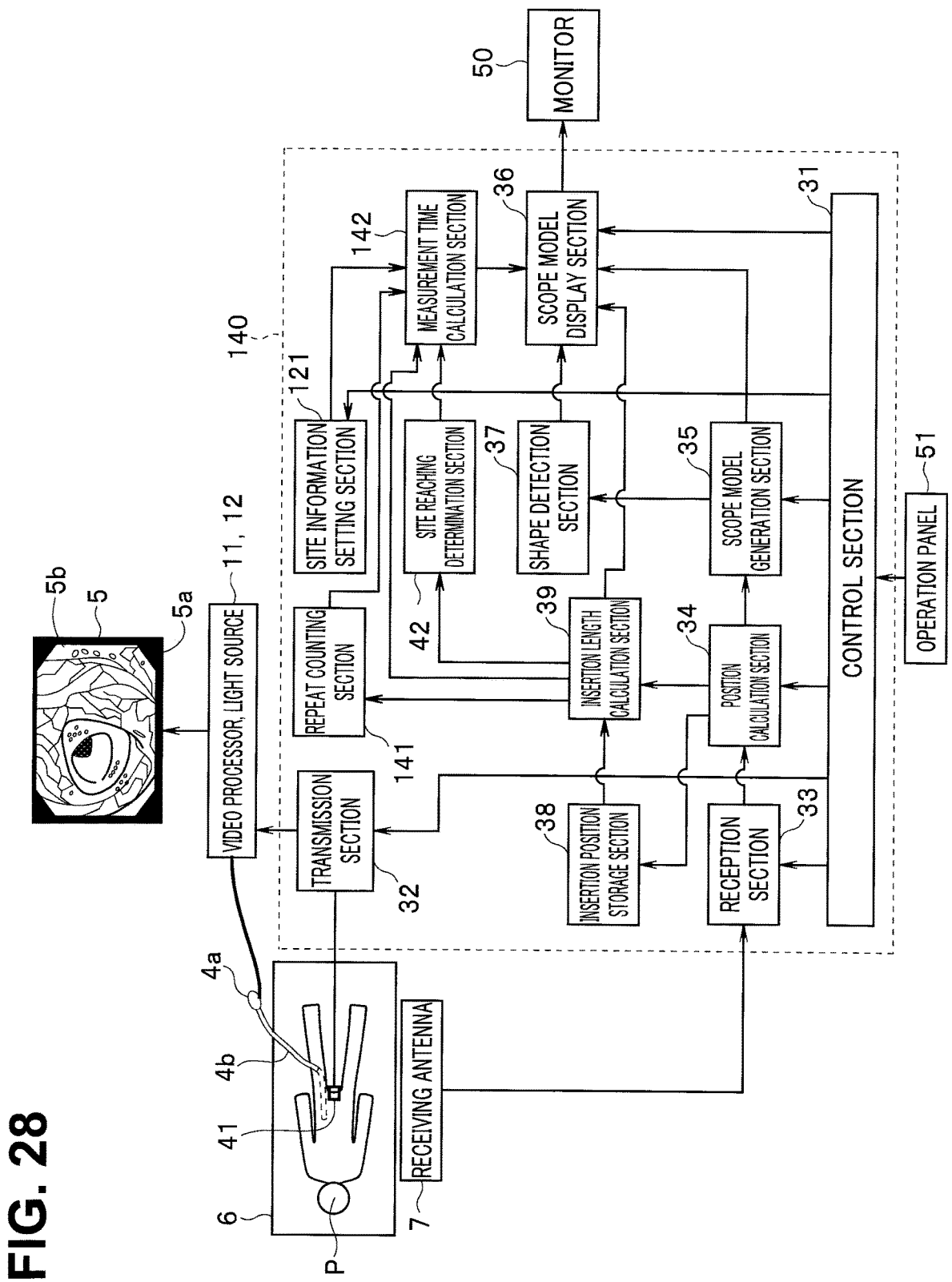
FIG. 28 is a block diagram illustrating an endoscope insertion observation apparatus according to an exemplary embodiment.

FIG. 28 is a block diagram illustrating another exemplary embodiment. In FIG. 28, the same constituent elements as those in FIG. 24 are attached with the same reference signs and descriptions thereof will be omitted.

When the insertion portion 4b is inserted into the intestinal tract, there is a case where insertion cannot be easily performed only by pushing the insertion portion 4b into the intestinal tract, since the intestinal tract includes flexed portions. Therefore, normally, the operator advances the insertion portion 4b toward the cecum by repeating pushing and pulling of the insertion portion 4b. Note that, also when the operator performs observation while extracting the insertion portion 4b from the cecum to the anus, the operator extracts the insertion portion 4b while pushing and pulling the insertion portion 4b. When the insertion is performed smoothly, it is considered that the number of times of pushing and pulling of the insertion portion 4b is smaller than a predetermined number of times (hereinafter, referred to as during-insertion upper limit number of times). In addition, when the observation is surely performed, the number of times of pushing and pulling of the insertion portion 4b is larger than a predetermined number of times (hereinafter, referred to as during-extraction lower limit number of times). In the present embodiment, the notification message is generated when the actual number of times of pushing and pulling of the insertion portion 4b is larger than the during-insertion upper limit number of times or smaller than the during-extraction lower limit number of times.

A control unit 140 in the present embodiment is different from the above embodiment shown in FIGS. 24-25B in that a repeat counting section 141 is additionally provided and a measurement time calculation section 142 is employed instead of the measurement time calculation section 122.

In the present embodiment, the during-insertion upper limit number of times and the during-extraction lower limit number of times of pushing and pulling at the time when the insertion portion moves between each of the sites are stored in the memory, not shown, in the site information setting section 121. Note that the control section 31 may enable the memory in the site information setting section 121 to store the information on the during-insertion upper limit number of times and the during-extraction lower limit number of times by the operation by the operator on the operation panel 51, for example.

Figures 29, 30:
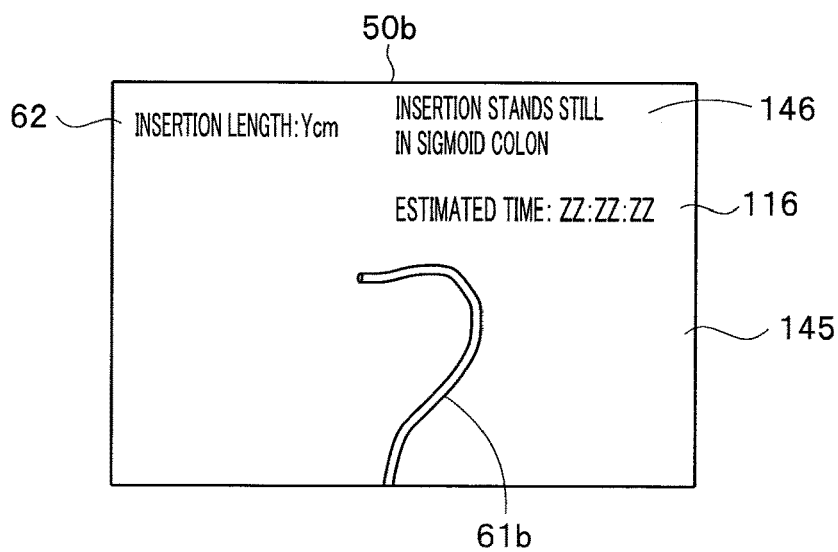
FIG. 29 is an explanatory diagram describing setting of a during-insertion upper limit number of times and a during-extraction lower limit number of times between each of sites corresponding to FIG. 25A.
FIG. 30 is an explanatory diagram illustrating a display example on a display screen of a monitor.

FIG. 29 is an explanatory diagram describing the setting of the during-insertion upper limit number of times between each of the sites corresponding to FIG. 25A and the setting of the during-extraction lower limit number of times between each of the sites corresponding to FIG. 25A. FIG. 29 shows the during-insertion upper limit number of times and the during-extraction lower limit number of times, which are set between each of the sites and stored in the memory in the site information setting section 121. The example in FIG. 29 shows that the length between the site V1 and the site V2 is 15 cm which is obtained by subtracting 15 cm from 30 cm, the during-insertion upper limit number of times for the insertion between the site V1 and the site V2 is set to 20, and the during-extraction lower limit number of times for the extraction between the site V1 and the site V2 is set to 15, for example.

As with the measurement time calculation section 122 in FIG. 24, the measurement time calculation section 142 is capable of calculating the insertion time and the observation time based on the insertion start signal, the site reaching signal, the extraction start signal, and the extraction end signal from the site reaching determination section 42.

The information on the insertion length is inputted from the insertion length calculation section 39 to the repeat counting section 141. The repeat counting section 141 detects that the insertion portion 4b is pushed and pulled based on the increase and decrease of the insertion length, counts the number of times of pushing and pulling, and outputs the counting result to the measurement time calculation section 142.

As with the measurement time calculation section 122 in FIG. 24, the measurement time calculation section 142 is capable of calculating the insertion time and the observation time based on the insertion start signal, the site reaching signal, an extraction start signal, and the extraction end signal from the site reaching determination section 42.

Furthermore, in the present embodiment, the measurement time calculation section 142 compares the upper limit value of the number of times (during-insertion upper limit number of times) of pushing and pulling during the insertion between each of the sites between the insertion start position and the target site and the lower limit value of the number of times (during-extraction lower limit number of times) of pushing and pulling during the extraction between each of the sites between the insertion start position and the target site with the actual number of times of pushing and pulling obtained by the repeat counting section 141, and causes the message corresponding to the result of comparison to be displayed on the display screen 50b of the monitor 50.

When the actual number of times of pushing and pulling, which is obtained based on the increase and decrease of the insertion length, is larger than the during-insertion upper limit number of times by a predetermined number (one, for example) or more, the measurement time calculation section 142 may cause a notification message "insertion stands still" etc., to be displayed.

In addition, when the actual number of times of pushing and pulling, which is obtained based on the increase and decrease of the insertion length, is smaller than the during-extraction lower limit number of times by a predetermined number (one, for example) or more, the measurement time calculation section 142 may cause the notification message "observation is insufficient" etc., to be displayed.

Next, operations in the embodiment thus configured will be described with reference to FIG. 30 by taking the colonoscopy as an example. FIG. 30 is an explanatory diagram illustrating a display example on the display screen of the monitor 50.

The operation that the measurement time calculation section 142 calculates the insertion time and the observation time based on the insertion start signal, the site reaching signal, the extraction start signal, and the extraction end signal from the site reaching determination section 42 and the operation that the measurement time calculation section 142 calculates the estimated time using the standard time between each of the sites are the same as those in the above embodiment shown in FIGS. 24-25B.

In the present embodiment, the repeat counting section 141 receives the information on the insertion length, and counts the number of times of pushing and pulling of the insertion portion between each of the sites based on the increase and decrease of the insertion length, and feeds the counting result to the measurement time calculation section 142.

The measurement time calculation section 142 compares the number of times of pushing and pulling of the insertion portion performed between each of the sites during the actual insertion with the during-insertion upper limit number of times, or compares the number of times of pushing and pulling of the insertion portion performed between each of the sites during the actual extraction with the during-extraction lower limit number of times. Then, if the actual number of times of pushing and pulling during the insertion is larger than the during-insertion upper limit number of times, for example, the measurement time calculation section 142 causes the notification message indicating that the number of times of pushing and pulling is relatively large to be displayed. In addition, if the actual number of times of pushing and pulling during the extraction is smaller than the during-extraction lower limit number of times, for example, the measurement time calculation section 142 causes the notification message indicating that the number of times of pushing and pulling is relatively small to be displayed.

For example, between the site V1 and the site V2 in FIG. 25A, that is, in the range of the sigmoid colon, it is supposed that the number of times of pushing and pulling of the insertion portion 4b during the insertion by the operator is equal to or larger than 21. Then, since the during-insertion upper limit number of times between V1 and V2, which is fed from the site information setting section 121, is 20, the measurement time calculation section 142 causes the message "insertion stands still" indicating that the number of times of pushing and pulling is large to be displayed, for example, when the number of times of pushing and pulling of the insertion portion 4b reaches 21.

FIG. 30 illustrates the display example in this case. As shown in FIG. 30, an insertion state display image 145 is displayed on the display screen 50b. The insertion state display image 145 includes the insertion shape image 61b. In addition, in the insertion state display image 145, the insertion length display 62 indicating that the current insertion length is Y cm, and the estimated time display 116 indicating the estimated time to reach the cecum are displayed.

FIG. 30 illustrates a display example of a message display 146 when the distal end of the insertion portion 4b is present between the site V1 and the site V2 in FIG. 25A, that is, in the sigmoid colon, for example. The measurement time calculation section 142 causes the message display 146 "insertion stands still", which indicates that the number of times of pushing and pulling at the time when the insertion portion moves from the site V1 to the site V2 is large, to be displayed on the display screen 50b of the monitor 50. This enables the operator to recognize that the insertion is not performed smoothly.

In addition, during the extraction of the insertion portion 4b, when the actual number of times of pushing and pulling of the insertion portion 4b between each of the sites is smaller than the during-extraction lower limit number of times, the measurement time calculation section 142 causes the notification message to be displayed when the number of times of pushing and pulling between the site V2 and the site V1 at the time when the distal end of the insertion portion 4b has passed through the site V1 is 13, for example. This enables the operator to recognize that sufficient observation is not performed.

The present embodiment is thus capable of obtaining the same effects as those in the above embodiment shown in FIGS. 21-25B, and enabling the operator to easily recognize that the number of times of pushing and pulling of the insertion portion is larger or smaller than the set number of times, to thereby enable effective support for the examination.

Note that, in the control units 10, 75, 80, 90, 100, 110, 117, 120, 130, and 140, the respective parts constituting these control units may be configured as individual electronic circuits or may be configured as circuit blocks in semiconductor circuits. In addition, each of the control units may be configured by including one or more CPUs. Furthermore, each of the control units may read a program for executing the functions of the respective parts from a storage medium such as a memory, and perform operations according to the read program.

The present disclosure is not limited to the above-described embodiments as they are, and may be embodied by modifying the constituent elements in a range without departing from the gist of the disclosure at the practical stage. In addition, the above-described embodiments and/or any of the plurality of constituent elements disclosed in the above-described embodiments may be combined. For example, the insertion state of the insertion portion can be detected by using any of the insertion length, the insertion shape, and the extracorporeal marker. In the embodiment configured to make a determination of whether or not the insertion portion has reached a site based on the insertion length, the determination of whether or not the insertion portion has reached a site may be made based on the insertion shape or by using a marker. That is, in the above-described embodiments, the insertion state may be obtained by using any of the methods. Furthermore, some constituent elements may be omitted from all of the constituent elements disclosed in the above-described embodiments, for example. In addition, the constituent elements over different embodiments may be appropriately combined.

What is claimed is:

1. An endoscope insertion observation apparatus comprising:
a processor configured to:
detect an insertion state of an insertion portion of an endoscope that is configured to be inserted into and extracted from a subject;
determine at least one of:
whether the insertion portion has reached a second site in the subject from a first site in the subject based on a result of the detection of the insertion state; and
whether the insertion portion has reached the first site from the second site in the subject based on a result of the detection of the insertion state;
calculate at least one of:
a duration of movement of the insertion portion from the first site to the second site after determining that the insertion portion has reached the second site; and
a duration of movement of the insertion portion from the second site to the first site after determining that the insertion portion has reached the first site; and
receive a signal indicating that the insertion portion has reached the first site or the second site from an external device, and
cause the external device to restart an external device calculation of the duration of movement of the insertion portion from the first site to the second site or the duration of movement of the insertion portion from the second site to the first site when the signal is received at a time different from a time when the processor determines that the insertion portion has reached the second site or the first site, respectively.

2. The endoscope insertion observation apparatus according to claim 1, wherein:
the first site is an insertion site at which insertion of the insertion portion into the subject is initiated,
the second site is a target site in the subject, and
the processor is configured to calculate the duration of movement from the first site to the second site as an insertion time.

3. The endoscope insertion observation apparatus according to claim 2, wherein the processor is also configured to calculate the duration of movement from the second site to the first site as an observation time.

4. The endoscope insertion observation apparatus according to claim 1, wherein:
the first site is a target site in the subject,
the second site is an extraction site at which extraction of the insertion portion from the subject is completed, and
the processor is configured to calculate the duration of movement of the insertion portion from the first site to the second site as an observation time.

5. The endoscope insertion observation apparatus according to claim 4, wherein the processor is configured to:
detect the insertion state by obtaining a position of the insertion portion, and
calculate the observation time such that a stopping time during which the insertion portion is stopped during the extraction is excluded from the observation time.

6. The endoscope insertion observation apparatus according to claim 1, wherein:
one of the first and second sites is an anus, and the other of the first and second sites is a cecum, and the processor is configured to calculate:
an insertion time for the insertion portion to reach the cecum from the anus; and
an observation time for the insertion portion to reach the anus from the cecum.

7. The endoscope insertion observation apparatus according to claim 1, wherein the processor is configured to:
detect the insertion state by:
obtaining a position of one or more parts of the insertion portion, and
calculating an insertion length of the insertion portion inserted in the subject based at least in part on the obtained position of the one or more parts of the insertion portion, and
determine the at least one of (i) whether the insertion portion has reached the first site, and (ii) whether the insertion portion has reached the second site based respectively on:
(i) a comparison between a first predetermined insertion length set for the first site and the calculated insertion length, and
(ii) a comparison between a second predetermined insertion length set for the second site and the calculated insertion length.

8. The endoscope insertion observation apparatus according to claim 1, wherein the processor is configured to:
detect the insertion state by:
obtaining a position of the insertion portion, and
calculating an insertion shape of the insertion portion inserted in the subject based at least in part on the obtained position of the insertion portion; and
determine the at least one of (i) whether the insertion portion has reached the first site, and (ii) whether the insertion portion has reached the second site based respectively on:
(i) a comparison between a first predetermined insertion shape of the insertion portion set for the first site and the calculated insertion shape of the insertion portion, and
(ii) a comparison between a second predetermined insertion shape of the insertion portion set for the second site and the calculated insertion shape of the insertion portion.

9. The endoscope insertion observation apparatus according to claim 1, wherein the processor is configured to:
detect the insertion state by obtaining:
a position of a distal end the insertion portion, and
a position near at least one of the first site and the second site based on an output of an extracorporeal marker disposed at the position near the at least one of the first site and the second site, and
determine the at least one of: (i) whether the insertion portion has reached the first site, and (ii) whether the insertion portion has reached the second site based respectively on:
(i) a comparison between the obtained position of the distal end of the insertion portion and the obtained position near the first site, and
(ii) a comparison between the obtained position of the distal end of the insertion portion and the obtained position near the second site.

10. The endoscope insertion observation apparatus according to claim 1, wherein the processor is further configured to change a result of the external device calculation based on a result of the calculation of the duration by the processor.

11. The endoscope insertion observation apparatus according to claim 1, wherein the processor is further configured to:
obtain a number of times that the insertion portion is pushed and pulled in a lumen of the subject into which the insertion portion is inserted based on an increase and a decrease of an insertion length of the insertion portion;
set an upper limit or a lower limit for the number of times that the insertion portion is pushed and pulled between predetermined sites in the lumen of the subject; and
determine whether or not the number of times that the insertion portion has been pushed and pulled exceeds the upper limit or the lower limit at each of the predetermined sites reached by the insertion portion, and cause a message indicating a result of the determination to be presented to an operator.

12. The endoscope insertion observation apparatus according to claim 11, wherein the processor is configured to:
detect the insertion state by:
obtaining a position of the insertion portion in the lumen of the subject, and
calculating the insertion length of the insertion portion in the lumen based at least in part on the obtained position of the insertion portion in the lumen.

13. An endoscope insertion observation apparatus comprising:
a processor configured to:
detect an insertion state of an insertion portion of an endoscope that is configured to be inserted into and extracted from a subject;
determine at least one of:
whether the insertion portion has reached a second site in the subject from a first site in the subject based on a result of the detection of the insertion state; and
whether the insertion portion has reached the first site from the second site in the subject based on a result of the detection of the insertion state;
calculate at least one of:
a duration of movement of the insertion portion from the first site to the second site after determining that the insertion portion has reached the second site; and
a duration of movement of the insertion portion from the second site to the first site after determining that the insertion portion has reached the first site;
calculate a moving speed of the insertion portion in a lumen in the subject based on a change in an insertion length of the insertion portion in the lumen;
set a length of the lumen of the subject; and
estimate a time for the insertion portion to reach at least one of the first site and the second site in the lumen, based on the moving speed of the insertion portion, the insertion length of the insertion portion, and the length of the lumen.

14. The endoscope insertion observation apparatus according to claim 13, wherein the processor is configured to set the length of the lumen based on subject information.

15. The endoscope insertion observation apparatus according to claim 13, wherein the processor is configured to:
detect the insertion state by:
obtaining a position of the insertion portion in the lumen of the subject, and calculating the insertion length of the insertion portion in the lumen based at least in part on the obtained position of the insertion portion in the lumen.

16. An endoscope insertion observation apparatus comprising:
a processor configured to:
detect an insertion state of an insertion portion of an endoscope that is configured to be inserted into and extracted from a subject;
determine at least one of:
whether the insertion portion has reached a second site in the subject from a first site in the subject based on a result of the detection of the insertion state; and
whether the insertion portion has reached the first site from the second site in the subject based on a result of the detection of the insertion state;
calculate at least one of:
a duration of movement of the insertion portion from the first site to the second site after determining that the insertion portion has reached the second site; and
a duration of movement of the insertion portion from the second site to the first site after determining that the insertion portion has reached the first site;
set predetermined sites in a lumen of the subject into which the insertion portion is inserted, the predetermined sites including the first site, the second site, and intermediate sites between the first site and the second site;
set a standard time required for movement of the insertion portion between each of the predetermined sites in the lumen;
measure a duration of movement of the insertion portion between each of the predetermined sites; and
calculate an estimated time for the insertion portion to reach the first site or the second site based on the standard time and the measured duration of movement of the insertion portion at each of the predetermined sites reached by the insertion portion.

17. The endoscope insertion observation apparatus according to claim 16, wherein the processor is further configured to:
calculate a difference between the standard time and the measured duration, and
cause, based on the calculated difference, a message related to the movement of the insertion portion to be presented to an operator.

18. The endoscope insertion observation apparatus according to claim 16, wherein the processor is configured to detect the insertion state by obtaining a position of the insertion portion in the lumen of the subject.

* * * * *